US012697306B2

(12) United States Patent
Duan et al.

(10) Patent No.: US 12,697,306 B2
(45) Date of Patent: Aug. 4, 2026

(54) ORALLY ADMINISTERED SOLID DOSAGE FORM DRUG

(71) Applicant: ASCENTAWITS PHARMACEUTICALS, LTD., Shenzhen (CN)

(72) Inventors: Jianxin Duan, Shenzhen (CN); Anrong Li, Shenzhen (CN)

(73) Assignee: ASCENTAWITS PHARMACEUTICALS, LTD., Shenzhen (CN)

(*) Notice: Subject to any disclaimer, the term of this patent is extended or adjusted under 35 U.S.C. 154(b) by 784 days.

(21) Appl. No.: 17/773,339

(22) PCT Filed: Oct. 30, 2020

(86) PCT No.: PCT/CN2020/125168

§ 371 (c)(1),
(2) Date: Apr. 29, 2022

(87) PCT Pub. No.: WO2021/083315

PCT Pub. Date: May 6, 2021

(65) Prior Publication Data

US 2022/0395464 A1 Dec. 15, 2022

(30) Foreign Application Priority Data

Nov. 1, 2019 (CN) ......................... 201911060861.8

(51) Int. Cl.
*A61K 9/48* (2006.01)
*A61K 31/664* (2006.01)

(52) U.S. Cl.
CPC .......... *A61K 9/4891* (2013.01); *A61K 9/4833* (2013.01); *A61K 9/485* (2013.01); *A61K 31/664* (2013.01)

(58) Field of Classification Search
CPC .... A61K 9/4891; A61K 9/4833; A61K 9/485; A61K 31/664
See application file for complete search history.

(56) References Cited

FOREIGN PATENT DOCUMENTS

| | | | | |
|---|---|---|---|---|
| WO | 2016145092 A1 | | 9/2016 | |
| WO | 2017087428 A1 | | 5/2017 | |
| WO | 2019062919 A1 | | 4/2019 | |
| WO | WO-2021008520 A1 | * | 1/2021 | ............ A61K 47/10 |

OTHER PUBLICATIONS

Di Martino et. al. Deuterium in drug discovery: progress, opportunities and challenges. Nature Reviews Drug Discovery. Springer Nature Limited 2023, 23 pages (Year: 2023).*

Kathryn Evans et al., OBI-3424, a Novel AKR1C3-activated Prodrug, Exhibits Potent Efficacy Against Preclinical Models of T-ALL, Clinical Cancer Research, Jul. 15, 2019, pp. 4493-4503, vol. 25, No. 14.

Kathryn Evans et al., The AKR1C3-activated Prodrug OBI-3424 Exerts Profound in Vivo Efficacy Against Preclinical Models of T-cell Acute Lymphoblastic Leukemia (T-ALL); a Pediatric Preclinical Testing Consortium Study, Oct. 2017, AACR-NCI-EORTC International Conference on Molecular Targets and Cancer Therapeutics.

Nogrady, Medicinal Chemistry A Biochemical Approach, 1985, pp. 388-392, Oxford University Press, New York.

Yinsheng Zhang, Development of Deuterated Drugs: Past, Present and Future, Progress in Pharmaceutical Sciences, Dec. 2017, pp. 902-918, vol. 41, No. 12.

* cited by examiner

*Primary Examiner* — Robert A Wax
*Assistant Examiner* — Olga V. Tcherkasskaya

(57) ABSTRACT

An orally administered solid dosage form comprising a drug for treating cancers, tumors or cell proliferative disorders contains a compound of the following structural formula I or II.

I

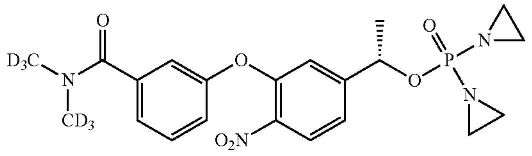

II

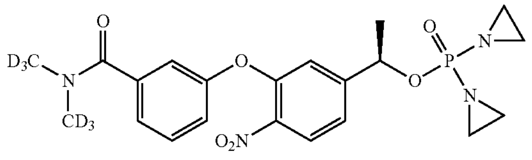

22 Claims, 3 Drawing Sheets

ORALLY ADMINISTERED SOLID DOSAGE FORM DRUG

BACKGROUND OF THE INVENTION

1. Field of the Invention

This disclosure relates to the research and development of solid preparations of compounds disclosed in PCT Patent Application No. PCT/US2016/021581 and Publication No. WO2016145092A1 corresponding to China Patent Application No 2016800150788 and Publication No. CN107530556A, and belongs to the field of researching and developing a preparation of cancer therapeutic compounds.

2. Description of the Related Art

AST-3424, a deoxyribonucleic acid (DNA) alkylating cancer therapeutic drug developed by our company targets an overexpressed aldehyde-ketone reductase 1C3 (AKR1C3). A DNA alkylating agent of the DNA alkylating cancer therapeutic drug AST-3424 can be referred to PCT application number PCT/US2016/021581 and a publication number WO2016/145092. A compound TH2870 corresponding to the DNA alkylating agent AST-3424 is disclosed in China application number CN2016800150788 and a publication number CN107530556A. (R)- and (S)-1-(3-(3-N,N-dimethylaminocarbonyl)phenoxyl-4-nitrophenyl)-1-ethyl-N,N'-bis(ethylene)phosphoramidate, compositions, a method using the same and a preparation thereof is disclosed in PCT application number PCT/US2016/062114 and a publication number WO2017087428A1. An S-configuration compound number TH3424 of the DNA alkylating agent is disclosed in China application number CN2016800446081 and a publication number CN108290911A. An R-S configuration of the compound TH3424 was subsequently prepared as a solid by our company. Then, a single crystal analysis was performed on the solid to determine that a configuration of TH3424 (AST-3424) is S-configuration, and a configuration of the corresponding TH3423 (AST-3423) is R-configuration. The name of TH3424 is (S)-1-(3-(3-N,N-Dimethylaminocarbonyl)phenoxy-4-nitrophenyl)-1-ethyl-N,N'-bis(ethylene) phosphoramidate, which is also known as OBI-3424 and an S-configuration compound of TH-2870. A CAS number of TH-3424 is 2097713-69-2, and a structure of AST-3424 is shown as follow.

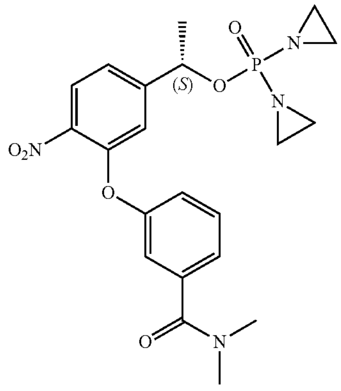

A chemical structual formula of AST-3424

There are profession authoritative documents that referring to Kathryn Evans, Jian Xin Duan, Tara Pritchard, etal. OBI-3424, a novel AKR1C3-activated prodrug, exhibits potent efficacy against preclinical models of T-ALL [J], Clinical Cancer Research, 2019, DOI: 10.1158/1078-0432.CCR-19-0551; Richard B. Lock, Kathryn Evans, Raymond Yung, Tara Pritchard, Beverly A. Teicher, Jian Xin Duan, Yuelong Guo, Stephen W. Erickson and Malcolm A. Smith, Abstract LB-B16: The AKR1C3-Activated Prodrug OBI-3424 Exerts Profound In Vivo Efficacy Against Preclinical Models of T-Cell Acute Lymphoblastic Leukemia (T-ALL); a Pediatric Preclinical Testing Consortium Study [C], AACR-NCI-EORTC International Conference: Molecular Targets and Cancer Therapeutics; Oct. 26-30, 2017; Philadelphia, PA, DOI:10.1158/1535-7163. The documents confirm that the compound is a broad-spectrum small molecule anti-cancer prodrug with curative effect on a variety of solid tumors and hematological tumors.

In order to conduct subsequent clinical trials, it is necessary to prepare suitable dosage forms for human administration, which are usually oral form or injectable form.

Since the compound is not a solid, but an oily substance. Although injections have been developed by our company in clinical trials, in some countries, such as the United States and Europe, local patients are reluctant to use the injections. Moreover, local doctors and pharmacists are more willing to prescribe oral solid dosage form to patients. It is because oral administration is convenient for patients to self-administer without going to medical institutions. It is cost a lot to ask medical staff to provide injection or intravenous drip administration. As well, for the doctors and pharmacists, a risk of oral administration is relatively small.

As a result, it is necessary to develop solid preparations.

SUMMARY OF THE INVENTION

To solve the mentioned-above technical problems, research and development (R&D) personnel of our company accidently discovered through experiments that a deuterated compound in which H at a specific position of AST-3424 is replaced by D which has better liver metabolism stability. Also, other pharmacodynamics and pharmacokinetic properties are similar to the AST-3424 compound with ordinary H atom, that is, a compound having the following structure:

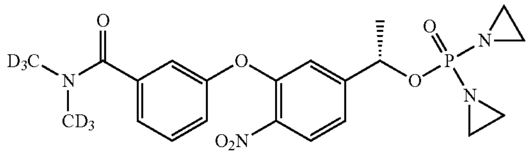

In a process of liver metabolism, the compound has better stability, and other properties are equivalent to AST-3424 with all H atoms. The deuterated compound at the specific position of the compound can attenuate a "first-pass effect" of a liver and thus are more suitable for administration as an oral dosage form.

To this end, following technical solutions are provided.

A First Technical Solution

An orally administered solid dosage form comprising a drug for treating cancers, tumors, and cell proliferative disorders comprises a compound having structural formula I or II shown below.

I

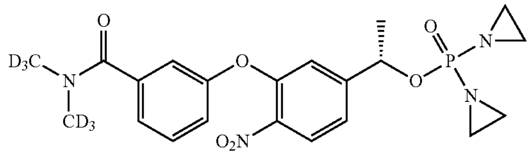

II

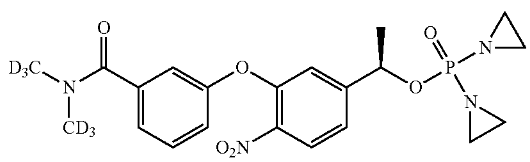

Further, the solid dosage form is a tablet. Obviously, the tablet is referred to an oral tablet which comprises an ordinary tablet, a sustained-release tablet, and so on. However, the tablet does not comprise a sublingual tablet of which active ingredients will enter the human blood circulation through the sublingual capillaries.

Further, a pH value of an aqueous solution or an aqueous dispersion of the tablet is greater than 6.8, more preferably 6.8 to 10.0.

The reason for such a pH value is that the solution of AST-3424 compound is found to be relative stable when the pH value is 6.8 or above. Accordingly, various excipients and raw materials are added to the tablet after formulation adjustment, so that the tablet presents the pH value automatically after dissolution.

Obviously, the tablet contains the compound of structural formula I or II and pharmaceutical excipients. Moreover, the compound of structural formula I or II is homogenously dispersed in the tablet, rather than encapsulated or laminated in the tablet.

The pharmaceutical excipients of the tablet comprise $NaCO_3$, $NaHCO_3$, NaOH, $KH_2PO_4$, and/or the pharmaceutical excipients comprise ethanol or propylene glycol.

Evidently, the compounds of $NaCO_3$, $NaHCO_3$, NaOH, $KH_2PO_4$ are alkaline in aqueous solution. The purpose is to ensure that AST-3424 is in an alkaline environment. The compounds listed here are only preferred and more suitable for clinical use. Apparently, other compounds such as KOH, $K_2CO_3$, $KHCO_3$, $NaH_2PO_4$, etc. are also equivalent.

Ethanol and propylene glycol are used to further dissolve and dilute AST-3424, which is convenient for preparation operations of active pharmaceutical ingredients (API) of a thick oily substance.

Further, as a preference, the solid dosage form is an enteric-coated tablet.

Obviously, the preceding ordinary tablet is designed to be alkaline for being able to stable in a gastric acid environment for a certain period after entering the stomach. Rather, the enteric-coated tablet is designed to not disintegrate in the stomach to release the drug, namely:

The enteric-coated tablet comprises an enteric coating and a tablet encapsulated therein. The encapsulated tablet comprises the compound having structural formula I or II and the pharmaceutical excipients.

The enteric-coated tablet is referred to a special tablet that does not disintegrate in gastric juice but can be disintegrated and absorbed in intestinal juice. It is usually coated with the enteric coating on the ordinary tablet.

The common enteric coating materials include shellac, cellulose acetate phthalate, seaweed gum, polyvinyl alcohol acetate phthalate, acrylic resin and hydroxypropyl methylcellulose phthalate. Additionally, a terpolymer of methyl methacrylate (MMA), methacrylic acid (MAA) and butyl acrylate (BA) and a new coating material Opadry (OPADRY® II, a trademark of Colorcon, UK) have shown broad prospects in enteric pharmaceutical preparations.

The pharmaceutical excipients of the enteric-coated tablet comprise $NaCO_3$, $NaHCO_3$, NaOH, or $KH_2PO_4$, and/or the pharmaceutical excipients comprise ethanol or propylene glycol.

Evidently, the compounds of $NaCO_3$, $NaHCO_3$, NaOH, $KH_2PO_4$ are alkaline in aqueous solution. The purpose is to ensure that AST-3424 is in an alkaline environment. The compounds listed here are only preferred and more suitable for clinical use. Apparently, other compounds such as KOH, $K_2CO_3$, $KHCO_3$, $NaH_2PO_4$, etc. are also equivalent.

Ethanol and propylene glycol here are to further dissolve and dilute AST-3424, which is convenient for the preparation operations of active pharmaceutical ingredients (API) of the thick oily substance.

In the enteric-coated tablet, a pH value of an aqueous solution or an aqueous dispersion of the tablet is greater than 6.8, more preferably 6.8 to 10.0.

As a preference, the solid dosage form is an enteric-coated capsule.

Evidently, the preceding enteric-coated tablet is coated with the enteric coating on the ordinary tablet. Also, the enteric-coated capsule contains granules containing the API drug filled in the enteric-coated capsule, namely:

The enteric-coated capsule comprises an empty enteric-coated capsule and a drug mixture filled therein.

Actually, the capsule shell of the enteric-coated capsule is made by adding special pharmaceutical polymer materials thereinto or specially processed, so as to make the enteric-coated capsule insoluble in gastric juice and only disintegrate and dissolve in intestinal juice. The enteric-coated capsule is not dissolved in the stomach, or in water or even in boiling water.

Usually, the enteric-coated capsule is made of gelatin and proper enteric-coated materials and can be divided in to an ordinary enteric-coated capsule and a colon-enteric-coated capsule. Nowadays, some new coating materials, such as cellulose acetate phthalate, polyvinyl acetate phthalate, polyvinylpyrrolidone, methylpropyl cellulose, acrylic resin and so on, are used in an industrial production of the enteric-coated capsule.

In the enteric-coated capsule, the filled drug mixture is a granule, and the granule contains the compound of structural formula I or II and the pharmaceutical excipients.

The pharmaceutical excipients of the enteric-coated capsule comprise $NaCO_3$, $NaHCO_3$, NaOH or $KH_2PO_4$, and/or the pharmaceutical excipients comprise ethanol or propylene glycol.

Evidently, the compounds of $NaCO_3$, $NaHCO_3$, NaOH, $KH_2PO_4$ are alkaline in aqueous solution. The purpose is to ensure that AST-3424 is in an alkaline environment. The compounds listed here are only preferred and more suitable for clinical use. Apparently, other compounds such as KOH, $K_2CO_3$, $KHCO_3$, $NaH_2PO_4$, etc. are also equivalent.

Ethanol and propylene glycol are used to further dissolve and dilute AST-3424, which is convenient for the preparation operations of API of the thick oily substance.

If the materials of the enteric-coated capsule contain gelatin, it is necessary to pay attention that the hydroscopicity of the granule is appropriate. Otherwise, the strong hydroscopicity of the granule will lead to dehydration, embrittlement, and rupture of the enteric-coated capsule.

In the enteric-coated capsule, a pH value of an aqueous solution or an aqueous dispersion of the tablet is greater than 6.8, more preferably 6.8 to 10.0.

As an option, the enteric-coated capsule comprises an empty soft enteric-coated capsule and a drug solution filled therein.

In the soft enteric-coated capsule, the drug solution contains the compound of structural formula I or II and a solvent. As well, the solvent is a mixed solvent of ethanol and propylene glycol.

In the soft enteric-coated capsule, a volume ratio of ethanol in the mixed solvent is not less than 50%.

In the soft enteric-coated capsule, the mixed solvent is composed of 75% ethanol and 25% propylene glycol by volume.

In the soft enteric-coated capsule, no water is added into the mixed solvent, and the water content is controlled within 0.5% by mass.

Clearly, the tumors, the cancers and the cell proliferative disorders in the disclosure comprise:

lung cancer, non-small cell lung cancer, liver cancer, pancreatic cancer, stomach cancer, bone cancer, esophagus cancer, breast cancer, prostate cancer, testicular cancer, colon cancer, ovarian cancer, bladder cancer, cervical cancer, melanoma, squamous-cell cancer, basal cell carcinoma, adenocarcinoma, squamous-cell carcinoma, sebaceous carcinoma, papillary carcinoma, papillary adenocarcinoma, cystadenocarcinoma, cystic carcinoma, medullary carcinoma, bronchial carcinoma, bone cell carcinoma, epithelial carcinoma, cholangiocarcinoma, choriocarcinoma, embryonic carcinoma, seminoma, Wilms' carcinoma, glioblastoma, astrocytoma, medulloblastoma, craniopharyngioma, ependymoma, pineal tumor, hemoblastoma, neurogenic tumor of the larynx, meningiomas, neuroblastoma of optic nerve, neuroblastomas, retinoblastomas, neurofibromas, fibroma sarcomatosum, fibroblastomas, fibroma, fibroadenomas, fibrochondromas, fibrocystic tumors, fibrous myxoma, osterfibroma, myxofibrosarcoma, fibropapillary, myxofibrosarcoma, bursal tumor, myxonchondroma, myxonchondrosarcoma, myxedema, myxoblastoma, liposarcoma, lipoma, lipoadenoma, lipoblastoma, lipochondroma, lipofibroma, lipoangioma, myxolipoma, chondrosarcoma, chondroma, chondromyoma, chordoma, chorioadenoma, chorioepithelioma, chorioblastoma, osteosarcoma, osteoblastoma, osteochondrofibroma, osteochondrosarcoma, osteochondroma, osteocystoma, cementoma, osteofibroma, fibrosarcoma, angiosarcoma, hemangioma, angiolipoma, angiochondroma, hemangioblastoma, angiokeratoma, angioglioma, hemangioendothelioma, angiofibroma, angiomyoma, angiolipoma, angiolymphoma, angiolipiomyoma, angiomyolipomas, angiomyoneuroma, angiomyxoma, angioreticuloendothelioma, lymphangiosarcoma, lymphogranuloma, lymphangioma, lymphoma, lymphomyxoma, lymphosarcoma, lymphangial fibrom, lymphocytoma, lymphoepithelioma, lymphoblastoma, endothelioma, endothelioblastoma, synovialoma, synovial sarcoma, mesothelioma, desmoplastic tumor, Ewing's tumor, leiomyoma, leiomyosarcoma, leioblastoma, leiomyofibroma, rhabdomyoma, rhabdomyosarcoma, rhabdomyomatous myxoma, acute lymphoblastic leukemia, acute myeloid leukemia, chronic disease cells, polycythemia, lymphoma, endometrial cancer, glioma, colorectal cancer, thyroid cancer, urothelial cancer or multiple myeloma.

A Second Technical Solution

A preparation method of the solid dosage form comprising a drug comprises operations as follow.

In a mixing and granulating operation, the pharmaceutical excipients, an ethanol solution of the compound having structural formula I or II, and an appropriate amount of water are mixed well and then granulated.

In a tableting operation, the granulated material is dried or not dried and then tableted to obtain tablets.

The tablets are coated to obtain enteric-coated tablets.

The granulated material is encapsulated into an empty capsule to obtain capsules.

A Third Technical Solution

The compound having structural formula I or II is provided:

I

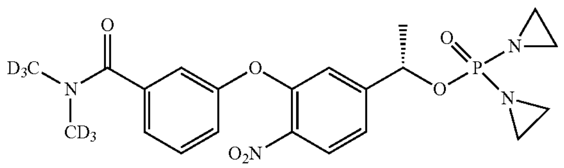

II

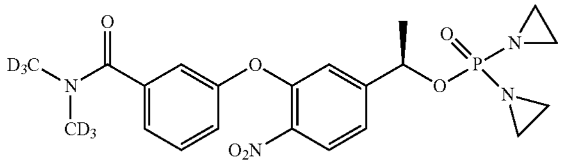

A Fourth Technical Solution

A use of the compound having structural formula I or II in preparation of an orally administered solid dosage form comprising a drug for treating the cancers, the tumors, or the cell proliferative disorders is provided:

I

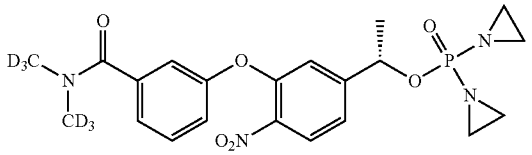

II

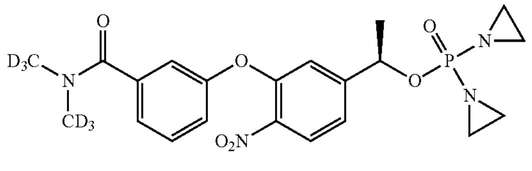

Apparently, the purpose here is mainly to prepare the tablets, the enteric-coated tablets, the hard enteric-coated capsules and the soft enteric-coated capsule, described above.

Each minimum administrable dosage unit of the solid dosage form comprising a drug contains 0.2, 0.5, 1.0 mg of the compound having structural formula I or II.

Specifically, for each dosage form, each tablet (for the ordinary tablet and enteric-coated tablet) or each capsule (for the hard enteric-coated capsule and the soft enteric-coated capsule) contains the compound having structural formula I or II with a mass of 0.2, 0.5, 1.0 mg. Absolutely, other contents can also be used, just according to the dosage, and the mentioned-above contents are more convenient to take.

A preparation method of the compound having structural formula I or II comprises reacting compounds III and IV with a compound V with or without participating of a base.

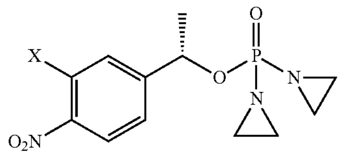

III

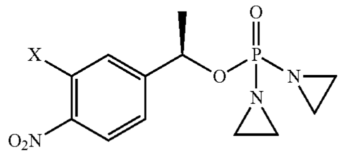

IV

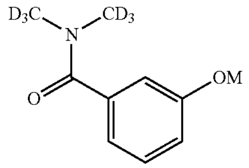

V

X is a halogen atom, which is preferably F. M is H, an alkali metal or alkaline earth metal.

The base mentioned here is generalized, which can be KOH, NaOH, $CH_3ONa$, NaH and other inorganic bases, or $K_2CO_3$, $KHCO_3$ and other alkaline salts.

It is necessary to use the base as an anti-acid agent to promote the reaction when M is H. Certainly, the reaction can be carried out without the base, but the reaction may be slower.

Since the present disclosure is to re-develop the formulation of AST-3424. Hence, the APIs of AST-3424 related to the present disclosure have been applied for patent applications, and the patent applications are listed as follow.

A DNA alkylating agent: Corresponding PCT application number PCT/US2016/021581 and a publication number WO2016/145092. A compound TH2870 corresponding to the DNA alkylating agent is disclosed in China application number 2016800150788 and a publication number 2016800150788.

(R)- and (S)-1-(3-(3-N,N-dimethylaminocarbonyl)phenoxyl-4-nitrophenyl)-1-ethyl-N,N'-bis(ethylene)phosphoramidate, compositions, a method using the same and a preparation thereof: Corresponding PCT application number PCT/US2016/062114 and a publication number WO2017087428A1, corresponding to China application number 2016800446081 and a publication number CN108290911A. Moreover, the above disclosures are incorporated into this specification.

In case of any difference or different definition concepts between the above applications and the specification, the specification shall prevail. If concepts or definitions in the specification are not clearly defined or limited, they shall be defined in accordance with the above applications. For other concepts and definitions not defined in the specification and the above applications, textbooks, manuals, etc. of organic chemistry, medical chemistry and pharmacy shall prevail.

With regard to the use in the specification, the drug produced may further comprise pharmaceutically acceptable adjuvants or excipients. The pharmaceutically acceptable adjuvants or excipients in the drug may comprise one or more of diluents, solubilizers, disintegrants, suspending agents, lubricants, binders, fillers, flavoring agents, sweeteners, antioxidants, surfactants, preservatives, encapsulation agents and pigments.

DESCRIPTION OF THE PREFERRED EMBODIMENTS

Figure 1:
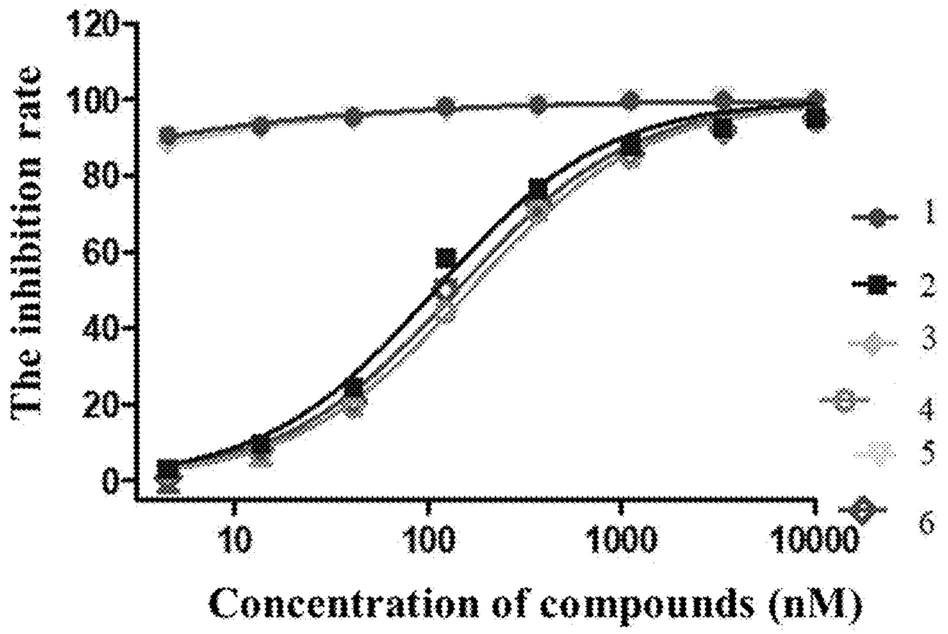
FIG. 1 is a cancer cell proliferation curve diagram of deuterated and non-deuterated AST-3424 under a condition of adding or not an inhibitor of AKR1C3 according to an embodiment of the present disclosure.

The present disclosure will be described below with reference to specific experimental data. It can be understood that these embodiments are only used to illustrate the present disclosure so that person having ordinary skill in the art can understand. As well, the embodiments do not limit the scope of the present disclosure on any approach.

Unless otherwise specified, the experimental methods in the following embodiments are conventional methods. Unless otherwise specified, the raw pharmaceutical materials, reagent, etc. in the following embodiments are all commercially available products.

Terms "patient" and "individual" are interchangeable and referred to mammals that need cancer treatment. Typically, the patient is a human. Specifically, the patient is a human diagnosed with cancer. In certain embodiments, the patient and the individual may refer to non-human mammals, for example non-human primates, dogs, cats, rabbits, pigs, mice or rats, used to select, characterize and evaluate drugs and therapies.

A term "prodrug" refers to a compound that is metabolized or transformed through other ways into a compound (or a medicine) with biological activity or higher activity after administration or application. The prodrug is chemically modified to make the prodrug less active or inactive relative to a drug. Nevertheless, the chemical modifications allow the corresponding medicine to be produced by metabolism or other biological processes after administrating the prodrug. The prodrug may have altered metabolic stability or delivery characteristics, fewer side effects, lower toxicity or improved flavor relative to the drug (for example, referring to reference Nogrady, 1985, Medicinal Chemistry A Biochemical Approach, Oxford University Press, New York, pages 388 to 392, which are incorporated in this specification by reference). Additionally, the prodrug can be synthesized by using reactants other than the corresponding medicine.

The term "solid tumor" refers to a metastatic tumor comprising, without limitation, bone, brain, liver, lung, lymph node, pancreas, prostate, skin, and soft tissue (sarcoma).

The term "therapeutically effective amount" of a drug refers to an amount of the drug that will have expected therapeutic effects when administered to a patient with cancer. It is worth to mention that the so-called expected therapeutic effects refer to alleviation, improvement, remission, or elimination of clinical manifestations of one or more cancers in patients. The expected therapeutic effects does not necessary have to occur by administration of one dose, and may only occur after administrating of a series of doses. Thus, the therapeutically effective amount can be administrated one or more times.

The term "treatment" of a condition of illness or the patient refers to taking approaches to achieve beneficial or expected results, including clinical results. For purposes of the present disclosure, the beneficial or expected results are indicated when any of the following conditions occur, but the present disclosure is not limited thereto. The conditions include alleviation of the disease degree; postponement or improvement of diseases progression; improvement, ease, or stabilization of disease state; or other beneficial results. In some cases, cancer treatment can result in a partial response or stabilizing the disease.

The term "tumor cells" refers to tumor cells of any suitable species like ma mMals, for instance rodent, canine, cats, horses, or human.

The preceding descriptions of the specific embodiments of the present disclosure do not limit the present disclosure. As well, person having ordinary skill in the art can make various modifications and changes according to the present disclosure, as long as the modifications and changes do not depart from the spirit of the present disclosure, which shall all belong to the scope of the claims of this disclosure.

Experiment 1: Studies on Solubility and Solution Stability of AST-3424 (all H Atoms)

1.1 Buffer/Solution Preparation

As long as the target concentration remains the same, a volume of stock solution and buffer different from that specified can be used.

A sodium hydroxide solution, 0.2 mol/L: 8.00 g of sodium hydroxide [NaOH] was taken and dissolved in water and diluted to 1000 ml with water.

A potassium dihydrogen phosphate solution, 0.2 mol/L: 27.22 g of potassium dihydrogen phosphate [$KH_2PO_4$] was taken and dissolved in water and diluted to 1000 ml with water.

An acetic acid solution, 2 mol/L: 114.4 ml of acetic acid was measured, diluted to 1000 ml with water and mixed well.

A boric acid and potassium chloride solution, 0.2 mol/L: 12.37 g of boric acid [$H_3BO_3$] and 14.91 g of potassium chloride [KCl] were taken and dissolved in water and diluted to 1000 ml with water.

An acetate buffer of pH 4.5: 2.99 g of sodium acetate [$NaC_2H_3O_2 \cdot 3H_2O$] was taken and placed in a 1000 ml-measuring flask. Then, 14.0 ml of the acetic acid solution was added, and water was added to a scale mark and mixed.

A phosphate buffer of pH 6.8: 50 ml of the potassium dihydrogen phosphate solution was placed in a 200 ml-measuring flask. Then, 22.4 ml of the sodium hydroxide solution was added, and water was added to a scale mark.

A phosphate buffer of pH 7.4: 50 ml of the potassium dihydrogen phosphate solution was placed in a 200 ml-measuring flask. Then, 39.1 ml of the sodium hydroxide solution was added, and water was added to the scale mark.

An alkaline borate buffer of pH 10.0: 50 ml of the boric acid and potassium chloride solution was placed in a 200 ml-measuring flask. Then, 43.7 ml of the sodium hydroxide solution was added, and water was added to the scale mark.

1.2 Solubility Study

An appropriate amount of AST-3424 (hereinafter called active pharmaceutical ingredients or API) was taken and placed in a suitable container containing 40 ml of the mentioned-above solutions (20 ml for organic solvents) respectively until excess oil droplets of AST-3424 existed in the solution.

Samples were put in a constant temperature shaking incubator at 25° C. and shaken at a proper speed (100 rpm). The samples were taken and checked pH values at each appointed time as specified in Table 1. Then, the samples were centrifuged (1000 rpm, 10 minutes), and added the corresponding solution or organic solvent (to dissolve the API for solubility study) to dilute to an appropriate concentration for HPLC analysis, so as to obtain solubility data. It should be noted that the dilution ratio after test was accurately recorded.

The solubility tests at 48 hours and 72 hours do not need to be checked if significantly decreased solubility was observed.

TABLE 1

Sampling appointed times and solubility test items

| Solution/Buffer | 1 h | 4 h | 8 h | 24 h | 48 h | 72 h |
|---|---|---|---|---|---|---|
| Ethanol | A | A | A | A | A | A |
| Propylene Glycol | A | A | A | A | A | A |
| Acetate buffer of pH 4.5 | A, P | A, P | A, P | A, P | A, P | A, P |
| Phosphate buffer of pH 6.8 | A, P | A, P | A, P | A, P | A, P | A, P |
| Phosphate buffer of pH 7.4 | A, P | A, P | A, P | A, P | A, P | A, P |
| Alkaline borate buffer of pH 10.0 | A, P | A, P | A, P | A, P | A, P | A, P |
| Purified water | A, P | A, P | A, P | A, P | A, P | A, P |

Remarks: A = Assay, to measure contents of AST-3424 in the solution;
P = pH 1.3 Solution Stability Study About 107.32 mg of AST-3424 (50% v/v, ethanol) was taken and placed in a 50 ml-measuring flask. Then, solvents which are an organic solvent, buffer solution or purified water, were respectively added to a scale mark. At each appointed time, 1 ml of samples was measured for HPLC analysis respectively. If the API was stable in the solution with the different pH values, a sampling appointed time was extended, for instance 5 days or more. The specific sampling appointed times and test items are shown in Table 2.

TABLE 2

Sample analysis times for solution stability study

| Solution/Buffer | 1 h | 4 h | 8 h | 24 h | 48 h | 72 h |
|---|---|---|---|---|---|---|
| Ethanol | A | A | A | A | A | A |
| Propylene Glycol | A | A | A | A | A | A |
| Acetate buffer of pH 4.5 | A, P | A | A | A | A | A, P |
| Phosphate buffer of pH 6.8 | A, P | A | A | A | A | A, P |
| Phosphate buffer of pH 7.4 | A, P | A | A | A | A | A, P |
| Alkaline borate buffer of pH 10.0 | A, P | A | A | A | A | A, P |
| Purified water | A, P | A | A | A | A | A, P |

Remarks: A= Assay, to determine contents of AST-3424 in solution, as well as peak purities and total impurities of HPLC;
P = pH 1.4 Test Method In the solubility study, for a determination of sample contents, 1 ml of culture medium were measured respectively, and then centrifuged at 1000 rpm for 10 minutes. Subnatant after centrifugation were collected respectively for high performance liquid chromatography (HPLC) analysis. In the solution stability study, the samples may be provided directly for HPLC analysis.

The contents were determined by a HPLC method: AST-3424 was used as an external standard for quantification.

A wavelength of UV diode-array detector (DAD) detector was 230 nm. C18 column was used at a temperature of 25° C.

Mobile Phase:

A: An ammonia acetate solution, 10 mmol/L: ammonia acetate was dissolved in a mixed solvent with a ratio of 95% water and 5% acetonitrile by volume.

B: An ammonia acetate solution, 8 mmol/L: ammonia acetate was dissolved in a mixed solvent with a ratio of 95% acetonitrile and 5% water by volume.

Subsequently, a gradient elution was performed.

1.5 Test Results

In Table 3, data of the solution stability of AST-3424 are summarized. The solution stability results of AST-3424 indicate that the API is stable for at least 72 hours in the ethanol, 1:1 solution of ethanol and propylene glycol, the buffer of pH 7.4, and the buffer of pH 10.0, respectively, under room temperature. The API is stable for at least 24 hours in the solution of pH 6.8 under room temperature. The API is unstable in the solution of pH 4.5 and water, especially in the acetate buffer of pH 4.5.

TABLE 3

Solution stability results of AST-3424 in different solution

| Solution | Test items | Sampling time points: 0 h | 1 h | 4 h | 8 h | 24 h | 48 h | 72 h |
|---|---|---|---|---|---|---|---|---|
| Ethanol | Content (mg/ml) | 1.238 | 1.280 | 1.246 | 1.240 | 1.240 | 1.278 | 1.236 |
| | pH value | — | — | — | — | — | — | — |
| Ethanol/ Propylene (50:50, v/v) glycol | Content (mg/ml) | 1.295 | 1.287 | 1.287 | 1.287 | 1.302 | 1.284 | 1.275 |
| | pH value | — | — | — | — | — | — | — |
| Acetate buffer of pH 4.5 | Content (mg/ml) | 0.673 | 0.413 | 0.218 | 0.093 | 0.013 | NA | NA |
| | pH value | 4.497 | — | — | — | — | — | 4.477 |
| Phosphate buffer of pH 6.8 | Content (mg/ml) | 1.202 | 1.200 | 1.193 | 1.185 | 1.168 | 1.145 | 1.102 |
| | pH value | 6.815 | — | — | — | — | — | 6.855 |
| Phosphate buffer of pH 7.4 | Content (mg/ml) | 1.267 | 1.266 | 1.266 | 1.262 | 1.262 | 1.249 | 1.228 |
| | pH value | 7.481 | — | — | — | — | — | 7.534 |
| Alkaline borate buffer of pH 10.0 | Content (mg/ml) | 1.265 | 1.165 | 1.261 | 1.258 | 1.261 | 1.257 | 1.242 |
| | pH value | 9.984 | — | — | — | — | — | 10.023 |
| Purified water | Content (mg/ml) | 1.186 | 1.126 | 1.056 | 1.005 | 0.918 | 0.860 | 0.810 |
| | pH value | 5.152 | — | — | — | — | — | 6.435 |

According to the solution stability results, AST-3424 is very unstable in the acetate buffer of pH 4.5. Therefore, the phosphate buffer of pH 6.8, the phosphate buffer of pH 7.4, the alkaline borate buffer of pH 10.0, and the purified water were selected for the solubility study. An appropriate amount of AST-3424 was weighed and placed in 40 ml of medium (8 ml ethanol/propylene glycol (50:50, v/v) was used), until excess flocci was present in the solution. If the solubility of the API in the aqueous solution is more than 2% (20 mg/ml), the API does not to be added more.

TABLE 4

The solution test results of AST-3424

| | Initial | Sampling time points and test items: 1 h | | 4 h | | 8 h | | 24 h | | 48 h | |
|---|---|---|---|---|---|---|---|---|---|---|---|
| Buffer/ Solution | pH of the solution | pH | Content (mg/mL) | pH | Content (mg/mL) | pH | Content (mg/mL) | pH | Content (mg/mL) | pH | Content (mg/mL) |
| Ethanol/ Propylene glycol (50:50, v/v) | — | — | 271.28 | — | 302.33 | — | 301.33 | — | 298.85 | — | 273.84 |
| pH 6.8 (Phosphate buffer) | 6.817 | 6.856 | 23.01 | 6.837 | 22.92 | 6.855 | 23.03 | 6.841 | 22.59 | 6.860 | 22.06 |

TABLE 4-continued

The solution test results of AST-3424

| | Initial | Sampling time points and test items | | | | | | | | | |
|---|---|---|---|---|---|---|---|---|---|---|---|
| | | 1 h | | 4 h | | 8 h | | 24 h | | 48 h | |
| Buffer/ Solution | pH of the solution | pH | Content (mg/mL) | pH | Content (mg/mL) | pH | Content (mg/mL) | pH | Content (mg/mL) | pH | Content (mg/mL) |
| pH 7.4 Phosphate buffer | 7.455 | 7.477 | 23.65 | 7.462 | 23.47 | 7.475 | 23.56 | 7.455 | 23.65 | 7.482 | 23.39 |
| pH 10.0 (Alkaline borate buffer) | 10.032 | 9.998 | 23.50 | 9.980 | 23.56 | 9.871 | 23.48 | 9.932 | 23.49 | 0.952 | 23.67 |
| Purified water | 6.169 | 5.004 | 20.92 | 5.651 | 20.12 | 5.971 | 19.68 | 6.378 | 18.83 | 6.512 | 17.79 |

The solubility of AST-3424 in the ethanol/propylene glycol (50:50, v/v) solution was greater than 270 mg/ml. The solubility of the API in the pH 6.8, the pH 7.4 and the pH 10.0 solutions were all about 23 mg/ml, and the solubility of the API in purified water is about 20 mg/ml. Since the API is unstable in the pH 6.8 solution and in the purified water, the solubility gradually decreased with time. At different times, the solution pH values of the API in the medium of pH 6.8, pH 7.4 and pH 10.0 remained unchanged. In the purified water containing the API, the pH values gradually increased from pH 5.004 to pH 6.512 within 48 hours.

1.6 Summary of Physical and Chemical Properties Related to the Solutions

The solubility was discussed firstly. The solubility of AST-3424 in the different solvents at 25° C. was summarized in Table 5. AST-3424 is easily soluble in alcohols solvents, such as the ethanol/propylene glycol. In particular, researchers also initially investigated other monohydric alcohols, such as methanol, propanol and butanol, as well as ethylene glycol, propylene glycol, glycerol, 1,3-butanediol, 1,2-butanediol, etc. These solvents all have good solubility for the API.

AST-3424 is sparingly soluble in the purified water, the pH 6.8 phosphate buffer, the pH 7.4 phosphate buffer, and the pH 10.0 alkaline borate buffer.

Additionally, AST-3424 is stable in the phosphate buffer of pH 7.4, but AST-3424 is less stable in the purified water and the phosphate buffer of pH 6.8. The inventors speculated that a three-membered ring structure containing nitrogen in AST-3424 is prone to ring-opening, hydrolysis, and deterioration in water. As a result, the water content should be minimized in the production and storage of injections.

TABLE 5

Solubility of AST-3424

| Descriptive terms | Solvents | Solubility (mg/ml) |
|---|---|---|
| Freely soluble (FS) | ethanol/propylene glycol (50:50, v/v) | 273.84 |
| Sparingly soluble (SPS) | Purified water | 17.79 |
| | pH 6.8 (Phosphate buffer) | 22.06 |
| | pH 7.4 (Phosphate buffer) | 23.39 |
| | pH 10.0 (Alkaline borate buffer) | 23.67 |

The preceding experiments proved that the solubility and pH stability of AST-3424, which provided the basis for selections of solid preparation excipients.

Experiment 2: Studies on Preformulation and Stability of AST-3424 Solution

Based on the stability of AST-3424 under alkaline conditions revealed in the above solubility and solution stability studies, solution formulation design, preparations, and stability studies of solutions were carried out.

2.1 Preformulation and Preparation

Investigations of AST-3424 drug preparation and preformulations comprise selecting various solvents and preparing different formulations.

After considering the toxicity of substances and the safety and availability of solvents of injections, the inventor team selected a prescription solvent comprising ethanol, propylene glycol, and tri-ethanolamine (an organic amine used to make a pH value alkaline) to prepare different formulations.

Then, depending on solubility, doses of 10 and 200 mg/mi were selected to prepare different formulations for study.

Subsequently, the stability study of the different formulations was performed at −20° C., 2-8° C., and 25° C.

The HPLC method was used to monitor the chemical properties of a product. The chemical properties comprise content, related substances, and enantiomeric excess values (EE values) to determine the optimal formulation of AST-3424.

Compositions (vol %) of the different formulations of 10 mg/ml of AST-3424 solutions were listed in Table 6 below.

TABLE 6

Compositions of the different formulations of AST-3424 solution (10 mg/ml)

| Formulations | Materials | | |
|---|---|---|---|
| | Ethanol (EtOH) | Propylene glycol (PG) | Tri-ethanolamine (Tris) |
| F1 | 100% | NA | NA |
| F2 | 99.5% | NA | 0.5% |
| F3 | 2% | 98% | NA |
| F4 | 2% | 97.5% | 0.5% |
| F5 | 25% | 75% | NA |
| F6 | 25% | 74.5% | 0.5% |
| F7 | 50% | 50% | NA |
| F8 | 50% | 49.5% | 0.5% |
| F9 | 75% | 25% | NA |
| F10 | 75% | 24.5% | 0.5% |
| F1-1 | 70% | 30% | NA |

Compositions (vol %) of the different formulations of 200 mg/ml of AST-3424 solution were listed in Table 7 below.

TABLE 7

Compositions of the different formulations of AST-3424 solution (200 mg/ml)

| Formulations | Materials Ethanol (EtOH) | Propylene glycol (PG) | Tri-ethanolamine (Tris) |
|---|---|---|---|
| F1 | 100% | NA | NA |
| F2 | 99.5% | NA | 0.5% |
| F3 | 50% | 50% | NA |
| F4 | 50% | 49.5% | 0.5% |
| F2-1 | 70% | 30% | NA |

AST-3424 dissolved in ethanol was weighed accurately and placed in a suitable measuring flask. Next, different solvents were added respectively to make final concentrations of the API to be 10 mg/ml or 200 mg/ml. The compositions of the different formulations were listed in Tables 3 and 4. 1 ml of bulk solutions were measured and poured into a 6 ml-Brown vials, respectively. After being sealed with rubber stoppers and aluminum caps, the drug preparations were stored at −20±2° C., 5±2° C., or 25±2° C., in the Brown lightproof vials, and at a humidity of 60±5% RH for different periods. At appointed times, samples were taken and examined. The test methods were the same as the solubility and solution stability of the first embodiment above.

2.2 Results of Stability Study

At each appointed time, the samples were taken out. Contents of API and related substances (i.e. impurities) in the samples were detected by HPLC. Sampling schedules in Tables 8 to Table 10 as follow were the analysis of the contents (peak area %) and stability study data of the related substances.

TABLE 8

Summary of stability study data of different formulations at 25° C. (±2° C.)

| Formulation | | 0 month Content % | 0 month Impurities % | 1 month Content % | 1 month Impurities % | 2 months Content % | 2 months Impurities % | 3 months Content % | 3 months Impurities % | 6 months Content % | 6 months Impurities % |
|---|---|---|---|---|---|---|---|---|---|---|---|
| AST- | F1 | 98.7 | 1.4 | 99.3 | 2.1 | 94.9 | 2.6 | 94.8 | 3.5 | 93.1 | 7.1 |
| 3424 | F2 | 98.6 | 1.4 | 100.2 | 3.6 | 95.0 | 5.6 | 88.8 | 8.0 | 80.1 | 14.9 |
| (10 | F3 | 96.1 | 1.3 | 97.0 | 2.5 | 91.1 | 3.8 | 87.0 | 5.9 | 88.7 | 6.7 |
| mg/ml) | F4 | 96.1 | 1.3 | 98.3 | 8.4 | 78.1 | 17.7 | 64.7 | 24.3 | 40.8 | 41.4 |
| | F5 | 97.9 | 1.3 | 98.6 | 2.4 | 94.8 | 3.6 | 89.3 | 5.8 | 88.0 | 6.1 |
| | F6 | 97.4 | 1.3 | 98.5 | 7.2 | 81.2 | 15.1 | 69.3 | 22.0 | 47.7 | 37.2 |
| | F7 | 98.8 | 1.4 | 100.3 | 2.3 | 93.8 | 3.1 | 89.6 | 4.1 | 89.0 | 6.1 |
| | F8 | 98.7 | 1.3 | 99.5 | 5.9 | 85.4 | 11.7 | 73.3 | 17.6 | 55.8 | 31.8 |
| | F9 | 98.7 | 1.4 | 100.3 | 2.0 | 96.6 | 2.7 | 90.9 | 3.5 | 91.1 | 4.9 |
| | F10 | 98.5 | 1.4 | 100.3 | 4.5 | 88.5 | 8.7 | 78.6 | 12.9 | 68.2 | 24.3 |
| | F1-1 | 100.9 | 1.2 | 100.5 | 1.8 | 95.4 | 2.6 | ND | ND | TBD | TBD |
| AST- | F1 | 98.2 | 1.3 | 101.9 | 1.6 | 99.5 | 1.1 | 92.0 | 2.8 | 91.8 | 4.5 |
| 3424 | F2 | 99.8 | 1.3 | 101.7 | 3.6 | 88.9 | 2.9 | 79.5 | 8.2 | 72.4 | 13.2 |
| (200 | F3 | 97.9 | 1.3 | 102.0 | 1.7 | 94.0 | 0.9 | 87.5 | 3.3 | 84.4 | 6.8 |
| mg/ml) | F4 | 97.4 | 1.5 | 100.7 | 9.6 | 73.0 | 5.1 | 62.0 | 18.5 | 47.5 | 21.1 |
| | F2-1 | 101.8 | 0.6 | 99.8 | 1.7 | 94.9 | 2.9 | ND | ND | TBD | TBD |

TABLE 9

Summary of stability study data of different formulations at 5° C. (2~8° C.)

| Formulation | | 0 month Content % | 0 month Impurities % | 1 month Content % | 1 month Impurities % | 2 months Content % | 2 months Impurities % | 3 months Content % | 3 months Impurities % | 6 months Content % | 6 months Impurities % |
|---|---|---|---|---|---|---|---|---|---|---|---|
| AST- | F1 | 98.7 | 1.4 | 99.0 | 1.3 | 99.2 | 1.3 | 99.7 | 1.2 | 96.9 | 1.4 |
| 3424 | F2 | 98.6 | 1.4 | 100.1 | 1.5 | 99.2 | 1.6 | 97.5 | 1.6 | 98.5 | 2.2 |
| (10 | F3 | 96.1 | 1.3 | 98.5 | 1.2 | 96.6 | 1.5 | 95.1 | 1.4 | 96.9 | 1.5 |
| mg/ml) | F4 | 96.1 | 1.3 | 97.6 | 1.3 | 95.6 | 2.6 | 92.6 | 3.2 | 91.4 | 5.3 |
| | F5 | 97.9 | 1.3 | 99.2 | 1.2 | 97.5 | 1.4 | 95.2 | 19.5* | 96.9 | 1.4 |
| | F6 | 97.4 | 1.3 | 99.2 | 1.8 | 96.4 | 2.2 | 92.7 | 2.8 | 93.0 | 4.4 |
| | F7 | 98.8 | 1.4 | 100.0 | 1.3 | 96.6 | 1.3 | 93.9 | 1.6 | 97.0 | 1.3 |
| | F8 | 98.7 | 1.3 | 99.0 | 1.6 | 96.3 | 1.3 | 93.8 | 2.3 | 95.2 | 3.6 |
| | F9 | 98.7 | 1.4 | 99.1 | 1.3 | 97.8 | 1.3 | 95.0 | 1.9 | 97.9 | 1.3 |
| | F10 | 98.5 | 1.4 | 100.6 | 1.5 | 98.0 | 1.3 | 95.0 | 1.9 | 97.9 | 1.3 |
| | F1-1 | 100.9 | 1.2 | 99.7 | 1.1 | 96.2 | 1.2 | ND | ND | TBD | TBD |
| AST- | F1 | 98.2 | 1.3 | 101.4 | 1.2 | 99.1 | 0.7 | 100.0 | 1.1 | 98.1 | 1.2 |
| 3424 | F2 | 99.8 | 1.3 | 100.1 | 1.3 | 98.7 | 0.6 | 07.1 | 1.6 | 102.5 | 2.3 |
| (200 | F3 | 97.9 | 1.3 | 100.0 | 1, 1 | 97.3 | 0.4 | 96.4 | 1.2 | 97.7 | 1.2 |
| mg/ml) | F4 | 97.4 | 1.5 | 1.5 | 99.6 | 95.9 | 0.8 | 92.6 | 2.8 | 88.1 | 6.1 |
| | F2-1 | 101.8 | 0.6 | 101.2 | 1.1 | 97.8 | 1.2 | ND | ND | TBD | TBD |

TABLE 10

Summary of stability study data of different formulations at −20° C. (−22~−18° C.)

| Formulation | | 0 month Content % | 0 month Impurities % | 1 month Content % | 1 month Impurities % | 2 months Content % | 2 months Impurities % | 3 months Content % | 3 months Impurities % | 6 months Content % | 6 months Impurities % |
|---|---|---|---|---|---|---|---|---|---|---|---|
| AST-3424 (10 mg/ml) | F1 | 98.7 | 1.4 | 99.3 | 1.1 | 96.4 | 1.2 | 96.0 | 1.1 | 95.9 | 1.2 |
| | F2 | 98.6 | 1.4 | 100.2 | 1.2 | 96.9 | 1.2 | 98.6 | 1.1 | 98.6 | 1.3 |
| | F3 | 96.1 | 1.3 | 97.0 | 1.2 | 95.7 | 1.2 | 99.2 | 1.1 | 98.6 | 1.2 |
| | F4 | 96.1 | 1.3 | 98.3 | 1.3 | 95.3 | 1.3 | 97.6 | 1.1 | 96.4 | 1.6 |
| | F5 | 97.9 | 1.3 | 98.6 | 1.2 | 95.9 | 1.1 | 96.8 | 3.2 | 96.7 | 1.2 |
| | F6 | 97.4 | 1.3 | 98.5 | 1.3 | 96.6 | 1.4 | 98.1 | 1.2 | 96.1 | 1.4 |
| | F7 | 98.8 | 1.4 | 100.3 | 1.2 | 96.8 | 1.2 | 97.3 | 1.5 | 97.5 | 1.1 |
| | F8 | 98.7 | 1.3 | 99.5 | 1.2 | 96.8 | 1.3 | 97.7 | 1.2 | 97.2 | 1.3 |
| | F9 | 98.7 | 1.4 | 100.3 | 1.2 | 98.5 | 1.1 | 98.4 | 1.1 | 98.0 | 1.1 |
| | F10 | 98.5 | 1.4 | 100.3 | 1.3 | 98.7 | 1.2 | 94.0 | 1.1 | 97.9 | 1.3 |
| | F1-1 | 100.9 | 1.2 | 101.9 | 1.1 | 96.4 | 1.1 | ND | ND | TBD | TBD |
| AST-3424 (200 mg/ml) | F1 | 98.2 | 1.3 | 101.9 | 1.1 | 101.3 | 0.8 | 99.2 | 1.1 | 99.9 | 1.1 |
| | F2 | 99.8 | 1.3 | 101.7 | 1.1 | 99.9 | 0.8 | 97.8 | 1.0 | 94.7 | 1.1 |
| | F3 | 97.9 | 1.3 | 102.0 | 1.1 | 98.0 | 0.5 | 97.1 | 0.9 | 97.4 | 1.0 |
| | F4 | 97.4 | 1.5 | 100.7 | 1.1 | 97.6 | 0.5 | 97.2 | 0.9 | 97.9 | 1.2 |
| | F2-1 | 101.8 | 0.6 | 101.9 | 1.0 | 98.0 | 1.2 | ND | ND | TBD | TBD |

The enantiomeric excess values (EE values) of the seven relatively stable formulations were measured and record in the following Table 11.

TABLE 11

EE % value for relatively stable formulations

| Condition of storage | Formulation | 0 month | 1 month | 2 months | 3 months | 6 months |
|---|---|---|---|---|---|---|
| 25° C. | F1 (10 mg/ml) | / | 97.86 | 97.85 | 97.89 | 97.86 |
| | F7 (10 mg/ml) | / | 97.85 | 97.85 | 97.91 | 97.89 |
| | F9 (10 mg/ml) | / | 97.85 | 97.84 | 97.90 | 97.87 |
| | F1-1 (10 mg/ml) | 97.84 | 97.91 | / | / | TBD |
| | F1 (200 mg/ml) | / | 97.63 | 97.55 | 97.62 | 97.67 |
| | F3 (200 mg/ml) | / | 97.69 | 97.68 | 97.62 | 97.57 |
| | F2-1 (200 mg/ml) | 97.84 | 97.89 | / | / | TBD |
| 2~8° C. | F1 (10 mg/ml) | / | 97.85 | 97.84 | 97.92 | 97.94 |
| | F7 (10 mg/ml) | / | 97.84 | 97.84 | 97.93 | 97.94 |
| | F9 (10 mg/ml) | / | 97.85 | 97.84 | 97.93 | 97.89 |
| | F1-1 (10 mg/ml) | 97.84 | 97.94 | / | / | TBD |
| | F1 (200 mg/ml) | / | 97.68 | 97.69 | 97.77 | 97.83 |
| | F3 (200 mg/ml) | / | 97.71 | 97.72 | 97.77 | 97.87 |
| | F2-1 (200 mg/ml) | 97.84 | 97.94 | / | / | TBD |
| −20° C. | F1 (10 mg/ml) | / | / | / | 97.95 | 97.93 |
| | F7 (10 mg/ml) | / | / | / | 97.95 | 97.92 |
| | F9 (10 mg/ml) | / | / | / | 97.95 | 97.89 |
| | F1-1 (10 mg/ml) | 97.84 | 97.97 | / | / | TBD |
| | F1 (200 mg/ml) | / | / | / | 97.79 | 97.84 |
| | F3 (200 mg/ml) | / | / | / | 97.81 | 97.85 |
| | F2-1 (200 mg/ml) | 97/84 | 97.97 | / | / | TBD |

Remark: "/" means no test;
"TBD" means not measured;
"*" means the bad data;
"ND" means lower than a detection limit of an instrument so as to not be measured;
"N/A" means not added or not contained 2.3 Results and Discussion The results of the stability of the different formulations of AST-3424 are shown in Tables 8 to Table 11. In the results of the stability of the different formulations stored at 25° C., the stability of the formulations is found to increase with the increasing proportion of ethanol in the formulations. Besides, the stability of the formulations with tri-ethanolamine is lower than that of the formulations without tri-ethanolamine.

Among the formulations at 10 mg/ml, F9 is the most stable formulation.

In the formulations stored at 2-8° C. and −20° C., the stability of the samples increased significantly. Further, compared with formulations stored at 2-8° C., the samples stored at −20° C. was more stable. Next, the EE values of the relatively stable formulations (i.e. F1 (10 mg/ml), F7 (10 mg/ml), F9 (10 mg/ml), F1-1 (10 mg/ml), F1 (200 mg/ml), F3 (200 mg/ml) and F2-1 (200 mg/ml)) were measured, and the EE values of the relatively stable formulations were shown in Table 11. The EE values of all formulations remained unchanged for 6 months under different storage conditions, indicating that there was no isomer transformation of active components in these formulations.

By comparing the results of stability study of the different formulations, it can be seen as follow.

Firstly, according to the results of formulations screening study in preceding Tables, with the increase of the proportion of ethanol in the formulations, the stability of the drug preparations increase. On the other hand, if tri-ethanolamine is added into the formulations, the drug preparations become unstable.

Secondly, the results of the stability study indicate that the storage temperature of the drug preparations at −20° C. is more stable than that at 2~8° C. or 25° C. Thus, the storage temperature has a significant effect on the stability of the drug preparations.

Thirdly, through a concentration screening of AST-3424 drug preparations, a candidate formulation with the code F9 is determined to be the most stable. The six-month results of the stability of the formulation F9 shows no significant changes in the related substances and the EE values.

Fourthly, according to the results of formulation investigations, the formulation F9 (75% of ethanol and 25% of propylene glycol) is selected as the final candidate formulation of a solution in soft capsules of AST-3424.

As stated in Experiments 1-2 above, it proved that as follow.

The pH values of the aqueous solutions or aqueous dispersions of the tablets are more than 6.8, more preferably 6.8 to 10.0.

It is more appropriate to select $Na_2CO_3$, $NaHCO_3$, NaOH, $KH_2PO_4$, ethanol or propylene glycol as the pharmaceutical excipients.

The content of the compound having structural formula I or II in the drug solution is 1-270 mg/ml.

The drug solution in the soft capsules contains the compound having structural formula I or II and a solvent, and the solvent is a mixed solvent of ethanol and propylene glycol. Furthermore, the mixed solvent is composed of 75% of ethanol and 25% of propylene glycol by volume and relatively stable, so that the soft capsules can be stored stably.

For the soft capsules, production method was divided into a compression method (molding method) and a dropping preparation method.

The Compression Method

The first step was to prepare a gel solution of capsule materials. According to formulas of the capsule materials, gelatin was soaked in distilled water to be swelled. Then, other materials were added together and stirred to mix evenly after the gelatin melted. The second step was to prepare a capsule film. The prepared gel solution was taken out and applied on a flat surface of a board to make it evenly thick. Next, the gel solution is heated at about 90° C. to evaporate the surface water and become the soft capsule film with certain toughness and elasticity. The third step was to compress the soft capsules. In small batch production, the soft capsules are made with a pill pressing mold manually. In mass production, an automatic rotary capsule rolling machine is often used to produce the soft capsules. The capsule film here was a modified gelatin, or other medical polymer materials were used directly. Therefore, it was ensured that the soft capsules did not disintegrate and release in the stomach, but disintegrates and releases in the intestinal tract.

The Dropping Preparation Method

The dropping preparation method is completed by a pill-dropping machine with a double-layer dripper. Gelatin-based soft capsule materials (commonly called as gel liquid) and medicine liquid flow out at different speeds in an outer layer and an inner layer of the double-layer dripper respectively, so that the quantitative gel liquid may wrap the quantitative medicine liquid. Then, the wrapped medicine liquid drops into a cooling liquid. Due to the action of surface tension, the wrapped medicine liquid becomes a sphere, and gradually cooled and solidified into the soft capsules, such as common cod liver oil capsules and so on.

The dropping preparation method refers to a method of preparing the soft capsules by a dropping machine. It is need to pay attention to the formulas and viscosity of the gel liquid, as well as the density and temperature of all the added solutions.

A preparation process of tablets mainly comprises the following operations.

In mixing and granulating operation, the pharmaceutical excipients, the compound having structural formula I or II in the ethanol solution (ethylene glycol was added as appropriate) and an appropriate amount of water were granulated after mixing well.

Obviously, the excipients comprise fillers (such as starch, dextrin, microcrystalline cellulose, etc.), lubricants, binders, disintegrants, etc. The excipients added in this granulating operation are only part of the formulation, and another part will be added in the tableting operation later.

Particularly, ethanol and water are added for moisturizing after mixing depended on the situation. In general, the amount of water added is as small as possible on the basis of being able to granulate. If possible, it is best not to add water, but to add ethanol, propylene glycol, or other substitutes to achieve the wetting effect. Besides, after adding water, the water content should be controlled within 0.5% by mass.

The excipients here comprise alkaline substances for adjusting pH, such as $Na_2CO_3$, $NaHCO_3$, NaOH, $KH_2PO_4$, etc.

In tableting operation, the granulated material is tableted after dried or without drying, an appropriate amount of the excipients are added and mixed evenly, and directly compressed to obtain the tablets. Additionally, the excipients in the tableting operation are fillers, lubricants, binders, disintegrants, etc.

The tablet is coated with an enteric coating to obtain an enteric-coated tablet. Commonly used enteric coating materials comprise cellulose acetate phthalate (CAP), polyvinyl alcohol phthalate (PVAP), methacrylic acid copolymer, cellulose acetate trimellitate (CAT), hydroxypropyl methyl cellulose phthalate (HPMCP), acrylic resin (sold under the trademark of Eudragit L100, Eudragit S100), etc.

The granulated materials are encapsulated into the enteric-capsules to obtain hard enteric-coated capsules.

Experiment 3: Comparison of Cancer Cell Inhibition In Vitro Between AST-3424 and AST-3424-D6 (i.e. a Compound of Structural Formula I)

The activities of the compounds were evaluated by a proliferation inhibition assay of active cancer cells in vitro.

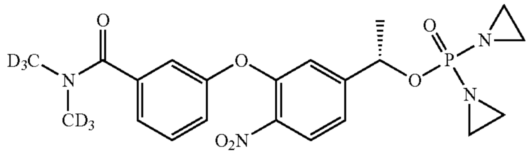

AST-3424-D6 (the compound of structural formula I)

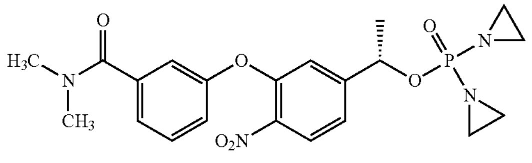

AST-3424

In vitro proliferation data for a human tumor cell line of H460 non-small cell lung cancer were reported in a Table of compounds below.

IC50 values were in nanomoles and were obtained by the following procedure. Cells were exposed in the compounds with different concentration for 2 hours. Next, the compounds were washed off, and fresh medium was added into plates. Afterwards, a growth rate and a cell-survival rate were obtained by cell staining and compared with a control treated with the medium only.

Specifically speaking, the exponentially growing cells were seeded in 96-well plates at a density of $4\times10^3$ cells/well, and incubated for 24 hours at 37° C. in 5 vol % $CO_2$, 95 vol % air and 100% relative humidity. Next, the compounds were added. Complementary, the compounds were dissolved in 100% DMSO at 200 times a desired final test concentration. The compounds were further diluted to 4 times the desired final test concentration with complete medium when the drug was added. A 50 μl aliquot of drug with the specific concentrations of the compounds was added to the 96-well plates already containing 150 μl of medium respectively to get the final test concentration reported. After the drug was added, the 96-well plates were incubated for 2 hours at 37° C. in 5 vol % $CO_2$, 95 vol % air and 100% relative humidity. Then, the drug was washed off, and the 96-well plates were incubated for 70 hours at 37° C. in 5% $CO_2$, 95% air and 100% relative humidity after adding the fresh medium. At the end of this incubation, Alamar Blue assay was used to quantify viable cells. The concentrations of the drug causing 50% growth inhibition (IC50) were calculated using computer software, and results are presented in a table below.

A cancer cell proliferation activity of the compounds with or without AKR1C3 enzyme inhibition was measured with and without adding TH3021 (with a sufficient inhibitory concentration), an inhibitor of AKR1C3.

Results are shown in Table 12, and FIG. 1 is obtained by plotting the original data.

TABLE 12

Cancer cell proliferation activity of deuterated and non-deuterated AST-3424 with and without AKR1C3 inhibitor

| Compound | IC50 (nmol) |
|---|---|
| AST-3424-D6 (curve 1 in FIG. 1) | <4.57 |
| AST-3424-D6 + TH3021 (curve 2 in FIG. 1) | 109.2 |
| AST-3424-D6 (curve 1 in FIG. 3) | <4.57 |
| AST-3424-D6 + TH3021 (curve 4 in FIG. 1) | 164.7 |
| AST-3424 (Reference) (curve 5 in FIG. 1) | <4.57 |
| AST-3424 + TH3021 (Reference) (curve 6 in FIG. 1) | 140.6 |

"Reference" is indicated the activity tested in the following applications.

A DNA alkylating agent of the DNA alkylating cancer therapeutic drug AST-3424 can be referred to PCT application number PCT/US2016/021581 and a publication number WO2016/145092. A compound TH2870 corresponding to the DNA alkylating agent is disclosed in China application number 2016800150788 and a publication number CN107530556A.

and the non-deuterated compound AST-3424 are similar, and there is no essential difference.

Experiment 4: Comparison of the Stability of Hepatomicrosome Between AST-3424 and AST-3424-D6 (i.e. The Compound of Structural Formula I)

The compounds, hepatomicrosome and reduced coenzyme NADPH were mixed together. Besides, a final concentration of the hepatomicrosome was 0.5 mg/ml, and human, male and mixed types of the hepatomicrosome were purchased. A final concentration of the NADPH was 2 mM. Next, the preceding mixtures were incubated in buffer (100 mM $KH_2PO_4$—$K_2HPO_4$) at 37° C. for 0, 5, 15, 30, 45, and 60 minutes, respectively. At the appointed incubation time, the reaction was terminated by the addition of an internal standard solution. Finally, the samples were centrifuged and the supernatant was taken for detection by LC-MS/MS.

Through mass spectrometry analysis, a concentration of the compounds in each sample was expressed by a peak-area ratio (a ratio of the peak-area of the compound to a peak-area of the internal standard). Then, each remaining percentage of the compounds (% Remaining) at each appointed incubation time was calculated with a reference that 0 minute at each concentration of the compounds. In logarithm of the remaining percentage was fitted linearly with the appointed incubation times, and a half-life and an intrinsic clearance were calculated according to the following formulas.

The remaining percentage (% Remaining)=(a peak area ratio at a certain appointed time ($PAR_{appointed\ time}$)/a peak area ratio at 0 minute ($PAR_{0\text{-}min}$)×100 (PAR: peak area ratio)

The elimination rate constant ($k$)=a negative of a slope (−gradient)

Half-life ($t_{1/2}$) (minutes)=0.693/$k$

In vitro clearance (CLint, in vitro) (ml/min/mg)=k/c (c: a concentration of hepatomicrosome in the incubation system)

TABLE 13

Stability test data of AST-3424 and AST-3424-D6 in human hepatomicrosome

| | % Remaining of AST-3424 | | | % Remaining of AST-3424-D6 | | |
|---|---|---|---|---|---|---|
| Time (minutes) | Sample 1 | Sample 2 | Average | Sample 1 | Sample 2 | Average |
| 0 | 101.36% | 98.64% | 100.00% | 101.60% | 98.40% | 100.00% |
| 5 | 77.67% | 80.00% | 78.83% | 85.07% | 87.20% | 86.13% |
| 15 | 45.83% | 47.38% | 46.60% | 62.93% | 60.00% | 63.47% |
| 30 | 17.86% | 16.93% | 17.40% | 36.80% | 34.93% | 35.87% |
| 45 | 6.52% | 6.95% | 6.74% | 21.17% | 21.07% | 21.12% |
| 60 | 2.64% | 2.68% | 2.66% | 13.52% | 12.75% | 13.13% |
| Stability parameter | k | | 0.0606 | k | | 0.0349 |
| | ($t_{1/2}$) (min) | | 11.44 | ($t_{1/2}$) (min) | | 19.86 |
| Correlation coefficient | $R^2$ | | 0.9987 | $R^2$ | | 0.9990 |

(R)- and (S)-1-(3-(3-N,N-dimethylaminocarbonyl)phenoxyl-4-nitrophenyl)-1-ethyl-N,N'-bis(ethylene)phosphoramidate, compositions, a method using the same and a preparation thereof is disclosed in PCT application number PCT/US2016/062114 and a publication number WO2017087428A1. An S-configuration compound number TH3424 of the DNA alkylating agent is disclosed in China application number 2016800446081 and a publication number CN108290911A.

Comparing FIG. 1 with Table 12, it can be seen that the in vitro activities of the deuterated compound AST-3424-D6

Figure 2:
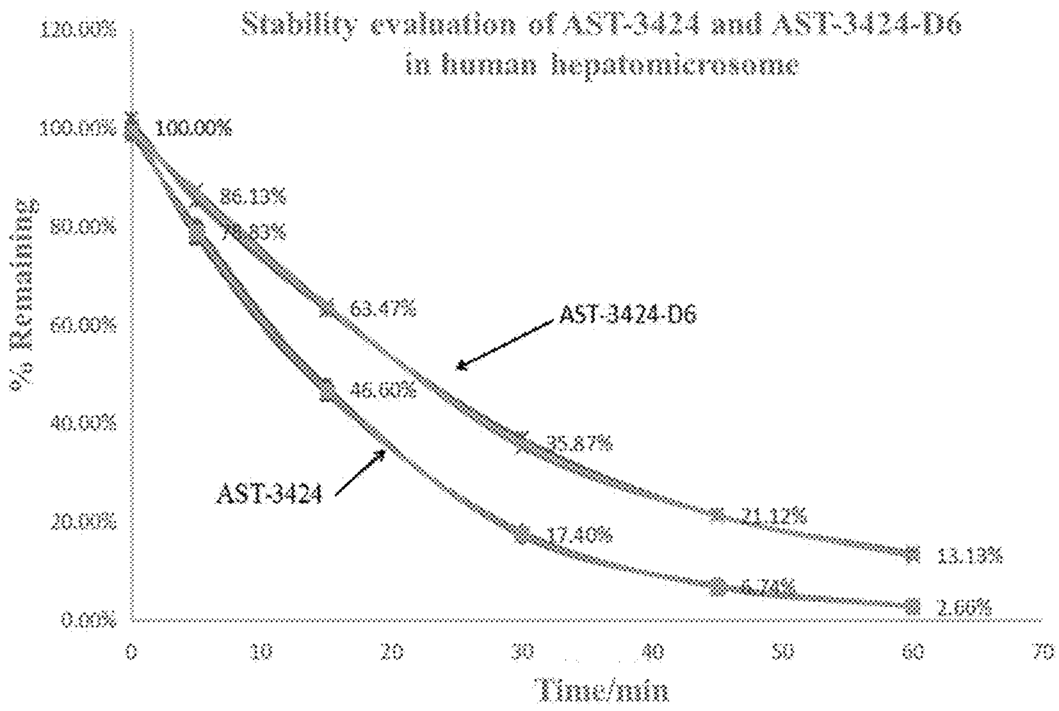
FIG. 2 is a time-concentration curve of hapatomicrosome metabolism of AST-3424-D6 and AST-3424 according to an embodiment of the present disclosure.

FIG. 2 was obtained by plotting the data in Table 13.

Comparing FIG. 2 and Table 13, it can be seen that curves of the hepatomicrosome of the deuterated compound AST-3424-D6 and non-deuterated compound AST-3424 are similar. However, it is distinct that AST-3424-D6 is more stable than the non-deuterated compound AST-3424. As well, at the same time period, the remaining percentage of AST-3424-D6 was at least 10% higher than that of AST-3424, which indicates that AST-3424-D6 has higher liver metabolism stability than AST-3424. Hence, AST-3424-D6 is more suitable for development as a dosage form for oral administration.

Experiment 5: Stability Study on Intravenous Infusion of AST-3424 and AST-3424-D6 (i.e. The Compound of Structural Formula I) into Living Animals AST-3424 and AST-3424-D6 (i.e. the compound of formula I) were administered to Philippine macaques by intravenous drip infusion, and blood samples were collected at different appointed times. Liquid Chromatograph-Mass Spectrometer/Mass Spectrometer (LC-MS/MS) was used to determine concentrations of the test substances in plasma of the Philippine macaques after administration, and relevant pharmacokinetic parameters were calculated.

5.1 Experimental Process

Preparation of Test Solutions

Preparation of Test Drug Solutions:

Dissolvent: 5 mass % glucose solution with pH 7.4

Preparation method: 0.447 ml of AST-3424 (0.2 mg/ml) and 0.481 ml of AST-3424-D6 (0.2 mg/ml) were added into 104.272 ml of the dissolvent, respectively, and mixed for 5 minutes to obtain colorless and clarified solutions with pH 7.0.

Animal Reception and Adaptation

The four male Philippine macaques were purchased from Guangxi Xiongsen Primate Development Experiment Co., Ltd. All Philippine macaques were healthy with qualified medical examination and no abnormality. Three of animals were used for the experiment, and one of them was used to prepare blank plasma.

Animal Administration

The 3 Philippine macaques were performed the experiment according to a table below.

5.2 Experimental Data Processing and Results

Pharmacokinetic Analysis

According to average blood concentration data of each group at each appointed time, the pharmacokinetic parameters of the compounds were respectively computed by a pharmacokinetic computing software, a non-compartmental model. In addition, the pharmacokinetic parameters were $AUC_{0-t}$, $AUC_{0-\infty}$, $MRT_{0-\infty}$, $C_{max}$, $T_{max}$, $t_{1/2}$, etc. In the case of the concentrations of the samples whose concentration being lower than a lower limit of quantification, the following schemes were used to compute the pharmacokinetic parameters. The samples sampled before reaching $C_{max}$ shall be computed as zero value, while the samples sampled after reaching $C_{max}$ shall be computed as non-quantifiable (marked as "BLQ").

Plasma-Drug Concentration

Figure 3:
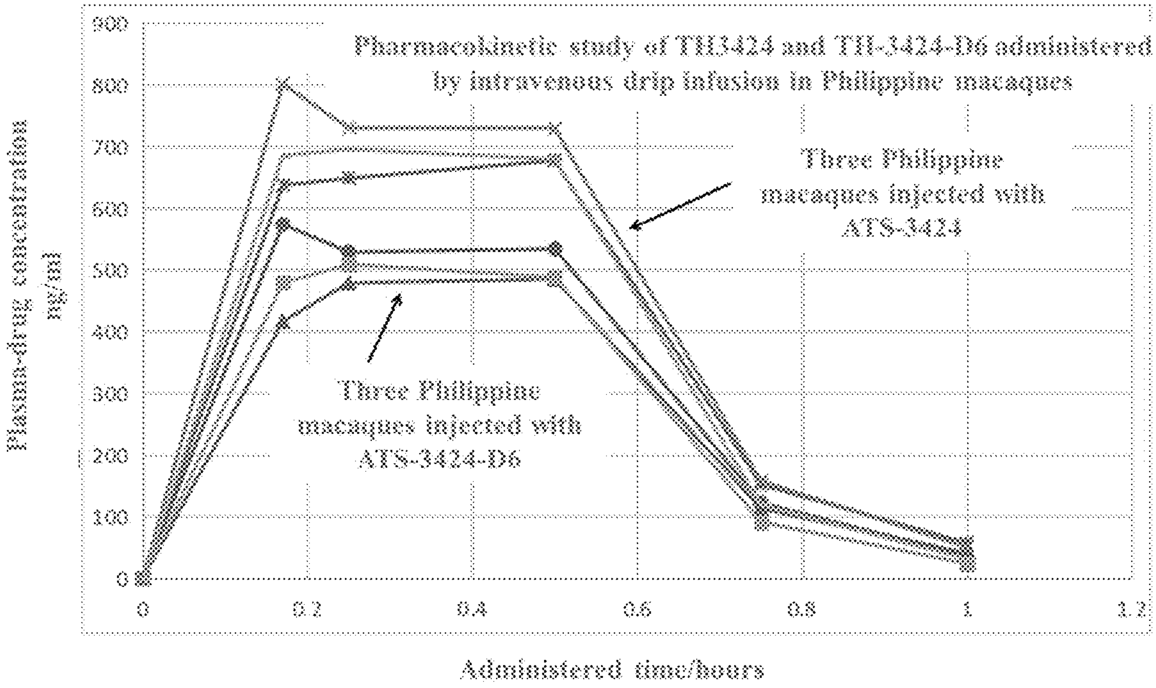
FIG. 3 is a graph of a drug concentration-time curve in plasma after administration of AST-3424-D6 and AST-3424 to Philippine macaques.

After a single intravenous infusion of the compounds AST-3424 and AST-3424-D6 was administered to the Philippine macaques, the whole blood samples of the corresponding animals were collected at the appointed times. Next, the whole blood samples were processed and biologically analyzed to obtain concentrations of the compounds in the plasma at the different appointed times. Results of the assay were listed in Table 14 below, and corresponding means of the plasma-drug concentration-time curves are shown in FIG. 3.

| | | Administration | | | | | |
|---|---|---|---|---|---|---|---|
| Group | Number Male | Compound | Compound dose (mg/kg) | Concentration of compound solution (mg/ml) | Administered volume (ml/kg) | Administered mode | Sample |
| 1 | 3 | AST-3424 and AST-3424-D6 | 1/Compound | 0.2 | 5 | Intravenous drip infusion | Plasma/Serum |

Sample Collection and Processing

About 0.8 ml of blood samples were collected through femoral vein and anticoagulated with heparin sodium. Appointed times of blood collection were before administration, 0.17, 0.25, 0.5, 0.75, 1, 2, and 4 hours after administration.

The blood samples were placed on ice after collection. Next, plasma samples were separated by centrifugation, and centrifugation conditions were 3500 rpm for 10 minutes at 4° C. Then, the collected plasma samples were stored at −80° C. until analysis. The plasma samples were analyzed by LC-MS/MS by an analysis department of an experimental institution. Besides, Lower limit of quantifications (LLOQ) of AST-3424 and AST-3424-D6 detection were 1 ng/ml. The accuracy of analysis results of an accompanying standard curve and a quality control samples all met the relevant requirements of biological analysis (the accuracy of the quality control samples exceeding 66.7% was between 85-115%) in a process of the sample detection.

After the experiment, the administered animals were returned to a reserve animal bank.

TABLE 14

Plasma concentrations of AST-3424 and AST-3424-D6 in Philippine macaques after single intravenous infusion administration

| Appointed | Plasma-drug concentration ( ng/ ml) | | | | |
|---|---|---|---|---|---|
| time (hr) | 101 | 102 | 103 | mean | SD |
| AST-3424-intravenous drip infusion −0.58 mg/kg | | | | | |
| 0 | No Peak | No Peak | No Peak | NA | NA |
| 0.17 | 637.50 | 800.80 | 685.96 | 708.09 | 83.87 |
| 0.25 | 648.75 | 729.91 | 695.61 | 691.42 | 40.74 |
| 0.5 | 677.40 | 729.08 | 679.80 | 695.43 | 29.17 |
| 0.75 | 151.51 | 157.68 | 118.92 | 142.70 | 20.83 |
| 1 | 57.31 | 50.63 | 31.86 | 46.60 | 13.19 |
| 2 | 1.29 | 1.51 | BLQ | 1.40 | NA |
| 4 | BLQ | BLQ | BLQ | NA | NA |
| AST-3424-D6- intravenous drip infusion −0.42 mg/kg | | | | | |
| 0 | No Peak | No Peak | No Peak | NA | NA |
| 0.17 | 416.49 | 573.76 | 478.95 | 489.73 | 79.19 |
| 0.25 | 478.66 | 528.54 | 508.71 | 505.30 | 25.11 |
| 0.5 | 484.93 | 533.71 | 487.88 | 502.17 | 27.35 |
| 0.75 | 113.12 | 122.04 | 91.24 | 108.80 | 15.85 |
| 1 | 40.95 | 36.24 | 24.30 | 33.83 | 8.58 |
| 2 | BLQ | BLQ | BLQ | NA | NA |
| 4 | BLQ | BLQ | BLQ | NA | NA |

Main Pharmacokinetic Parameters

According to the plasma-drug concentration data of each drug group, the pharmacokinetic parameters of each compound group were computed using the non-compartmental model of the pharmacokinetic computing software. The pharmacokinetic parameters were shown in Table 15.

Table 15: Main pharmacokinetic parameters of AST-3424 and AST-3424-D6 in the plasma after single intravenous infusion in Philippine macaques concentrations (both were 0.31 hours) are identical, the elimination half-lives (one was 0.16 hours, the other was 0.12 hours) are closed, and the retention times (one was 0.17±0.03 hour, the other was 0.14±0.01 hours) are also closed.

Further, referring to FIG. 3, we can see that metabolism curves of the deuterated compound AST-3424-D6 (TH3424-D6) and the non-deuterated compound AST-3424 (TH3424) in the blood samples are similar. However, it is obvious that

TABLE 15

Main pharmacokinetic parameters of AST-3424 and AST-3424-D6 in the plasma after single intravenous infusion in Philippine macaques

| Unit<br>Parameters | hr<br>$T_{1/2}$ | hr<br>$T_{max}$ | ng/mL<br>$C_{max}$ | hr*ng/mL<br>$AUC_{(0-t)}$ | hr*ng/mL<br>$AUC_{(0-\infty)}$ | mL/kg<br>Vz | mL/hr/kg<br>Cl | hr<br>$MRT_{(0-t)}$ | hr<br>$MRT_{(0-\infty)}$ | mL/kg<br>$V_{ss}$ |
|---|---|---|---|---|---|---|---|---|---|---|
| AST-3424-0.58 mg/kg | | | | | | | | | | |
| 101 | 0.18 | 0.50 | 677.40 | 430.42 | 430.76 | 353.58 | 1346.47 | 0.19 | 0.19 | 261.23 |
| 102 | 0.19 | 0.17 | 800.80 | 474.63 | 475.04 | 333.43 | 1220.95 | 0.17 | 0.18 | 213.73 |
| 103 | 0.11 | 0.25 | 695.61 | 404.18 | 409.39 | 231.47 | 1416.75 | 0.13 | 0.14 | 201.53 |
| Mean | 0.16 | 0.307 | 724.60 | 436.41 | 438.39 | 306.16 | 1328.06 | 0.17 | 0.17 | 225.50 |
| Standard deviation (SD) | 0.04 | 0.172 | 66.62 | 35.60 | 33.49 | 65.46 | 99.19 | 0.03 | 0.03 | 31.54 |
| AST-3424-D6-0.58 mg/kg | | | | | | | | | | |
| 101 | NA | 0.50 | 484.93 | 285.67 | NA | NA | NA | 0.15 | NA | NA |
| 102 | 0.13 | 0.17 | 573.76 | 327.39 | 334.13 | 233.68 | 1256.99 | 0.14 | 0.16 | 197.79 |
| 103 | 0.12 | 0.25 | 508.71 | 291.62 | 295.67 | 236.79 | 1420.48 | 0.14 | 0.15 | 207.06 |
| Mean | 0.12 | 0.31 | 522.46 | 301.56 | 314.90 | 235.24 | 1338.73 | 0.14 | 0.15 | 202.43 |
| Standard deviation (SD) | NA | 0.17 | 45.99 | 22.57 | 27.19 | NA | NA | 0.01 | NA | NA |

Remark:
(1) Calculation software Phoenix Winnolin 7.0-non-compartmental model
(2) PK parameters prescriptions
$AUC_{(0-t)}$: an area under the plasma-drug concentration-time curve from 0 to t
$AUC_{(0-\infty)}$: an area under the plasma-drug concentration-time curve from 0 to ∞
$C_{max}$: maximum plasma concentration
$T_{max}$: time of maximum plasma concentration
$T_{1/2}$: half-life
$MRT_{(0-t)}$: the average retention time in a period from 0 to t
$MRT_{(0-\infty)}$: the average retention time in a period from 0 to ∞
CL: clearance rate
$V_{ss}$: volume of distribution at steady-state
Vz: volume of distribution of statistical moment parameter
NO Peak: no chromatographic peak was detected, and it was regarded as zero
NA: not applicable
101/102/103 are the numbers of the three animals Results Both AST-3424 and AST-3424-D6 were administered at a dose of 1 mg/kg, and at the concentration of 0.2 mg/ml. By analyzing drug solutions, an actual concentration of AST-3424 was 0.117 mg/ml, and an actual concentration of AST-3424-D6 was 0.085 mg/ml. As well, an actual dose of AST-3424 was 0.58 mg/kg, and an actual does of AST-3424-D6 was 0.42 mg/kg.

After the Philippine macaques were administered 0.58 mg/kg of AST-3424, an average time to a peak concentration was 0.31 hours (Cmax was 724.60±66.62 ng/ml), an average elimination half-life ($t_{1/2}$) was 0.16 hours, AUC(0-t) was 436.41±35.60 h*ng/ml, AUC(0-∞) was 438.39±33.49 h*ng/ml, MRT(0-t) was 0.17±0.03 hours, and MRT(0-Co) was 0.17±0.03 hours.

After the Philippine macaques were administered 0.42 mg/kg of AST-3424-D6, an average time to a peak concentration was 0.31 hours (Cmax was 522.46±45.99 ng/ml), an average elimination half-life ($t_{1/2}$) was 0.12 hours, AUC(0-t) was 301.56±22.57 h*ng/ml, AUC(0-∞) was 314.90±27.19 h*ng/ml, MRT(0-t) was 0.14±0.01 hours, and MRT(0-∞) was 0.15 hours.

By comparing the relevant pharmacokinetic parameters, it can be apparently seen that the average time to the peak an integral area under an AUC line of the drug-time curve of AST-3424-D6 is smaller than that of the non-deuterated compound AST-3424. That is, an exposure of AST-3424-D6 in the blood circulation system is less than that of AST-3424 in the blood circulation system. Accordingly, AST-3424-D6 has little toxicity to the blood circulation system. As a result, AST-3424 is more suitable for development as an injection than AST-3424-D6, while AST-3424-D6 is more suitable for development as an oral drug for the treatment of solid tumors than AST-3424. Besides, the solid tumors are tumors excluding blood tumors, and the blood tumors are various leukemia, for example.

Based on the above experiments and combined with a person having ordinary skill in the art, it can be known that the compound of AST-3424-D6 with S-configuration and the compound of AST-3424-D6 with R-configuration have similar properties and conclusions as follow. The metabolism curves of the deuterated compound AST-3424-D6 (TH3424-D6) and the non-deuterated compound AST-3424 (TH3424) in the blood samples are similar. However, it is obvious that an integral area under an AUC line of the drug-time curve of AST-3424-D6 is smaller than that of the non-deuterated compound AST-3424. That is, an exposure of AST-3424-D6 in the blood circulation system is less than that of AST-3424 in the blood circulation system. Accordingly, AST-3424-D6 has little toxicity to the blood circulation system. As a result, AST-3424 is more suitable for development as an injection than AST-3424-D6, while AST-3424-D6 is more suitable for development as an oral drug for the treatment of solid tumors than AST-3424. Besides, the solid tumors are tumors excluding blood tumors, such as various leukemia.

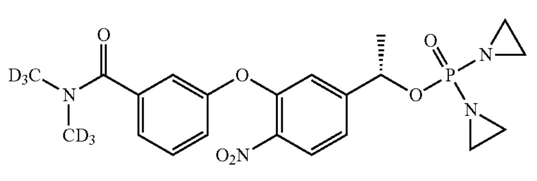

AST-3424-D6, S-configuration, structural formula I

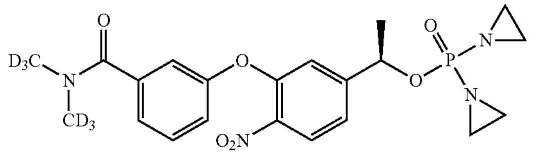

AST-3424-D6, R-configuration, structural formula II

Experiment 6: Synthesis of AST-3424-D6 (i.e. The Compound of Structural Formula I)

6.1 Synthesis Route

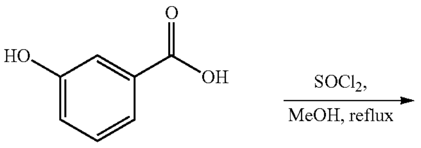

AST-3424-D6-A

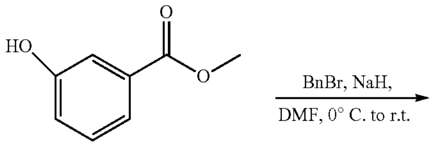

AST-3424-D6-B

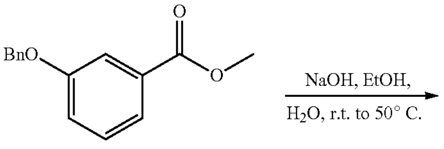

AST-3424-D6-C

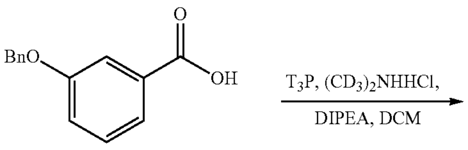

AST-3424-D6-D

-continued

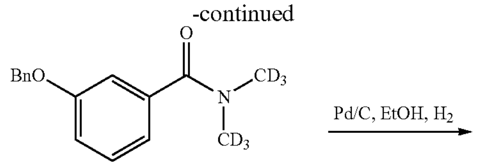

AST-3424-D6-E

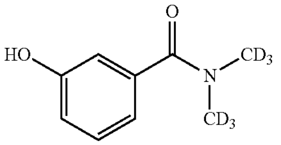

AST-3424-D6-F

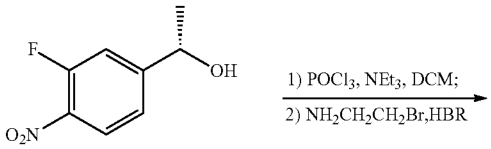

AST-3424-D6-H

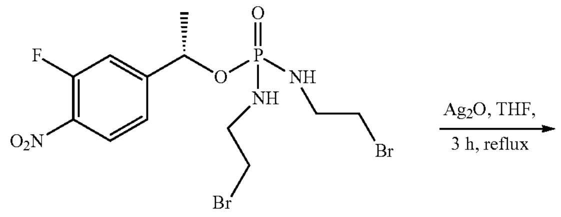

AST-3424-D6-I

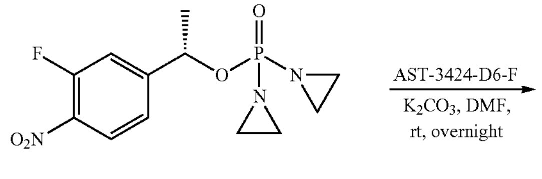

AST-3424-D6-J

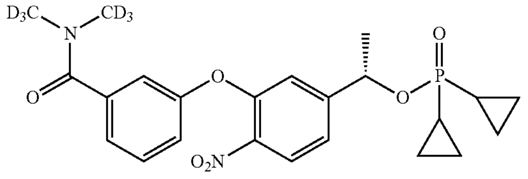

AST-3424-D6

6.2 Synthesis Steps

Synthesis of AST-3424-D6-B

AST-3424-D6 (6 g, 0.217 mol) was dissolved in anhydrous methanol (300 ml), which was heated to reflux. Next, sulfoxide chloride (51.7 g, 0.335 mol) was added. After addition, a reaction was completed by stirring under reflux for 6 hours. Thionyl chloride was concentrated off, and the residue was dissolved in ethyl acetate (200 ml), and then washed with water, washed with brine, dried, and concentrated. A pure product (30.4 g, 92.1%) was obtained by mashing with methyl tert-butyl ether (MTBE) as a white solid. $^1H$-NMR (400 MHz, $CDCl_3$): δ7.59-7.61 (m, 2H), 7.29-7.33 (m, 1H), 7.07 (d, J=7.6 Hz, 1H), 5.04 (brs, 1H), 3.92 (s, 3H). MS: 153.0 $[(M+1)^+]$.

Synthesis of AST-3424-D6-C

Under nitrogen protection, AST-3424-D6-B (15 g, 98.6 mmol) was dissolved in DMF (200 ml), which was cooled to 0° C. Next, NaF (7.9 g, 197.2, 60%) was added in batches, and kept at 0° C. for one hour. After benzyl bromide (25.1 g, 147.9 mmol) was added dropwise, the reaction was completed by stirring at room temperature for one hour. Then, after cooling to 0° C., saturated aqueous ammonium chloride solution (50 ml) was added dropwise, extracted with ethyl acetate (100*3 ml), washed with brine, dried, and concentrated. A crude product (26.0 g, quantitative) was obtained as a white solid, and was used directly in the next step.

Synthesis of AST-3424-D6-D

The AST-3424-D6-C crude product (26 g) obtained above was added into a mixed solution of water and ethanol (100 ml: 100 ml). Next, after solid sodium hydroxide (11.8 g) was added in batches, the mixture was stirred at 50° C. overnight. After the reaction was completed, the mixture was cooled to 0-5° C. Then, 6 N hydrochloride acid solution was added dropwise into the cooled mixture to adjust pH to acidity, and a large amount of white solid was precipitated. The white solid was suction filtered, washed with water, and dried to obtain a pure product (20.8 g, yield 92.4%) as white powder. $^{1}$H-NMR (400 MHz, DMSO-$d_6$): δ13.03 (brs, 1H), 7.25-7.54 (m, 9H), 5.16 (s, 2H), MS: 226.9[$(M-H)^-$], Synthesis of AST-3424-D6-E Under nitrogen protection, AST-3424-D6-D (7.1 g, 31.1 mmol) and deuterated dimethylamine hydrochloride (3 g, 34.3 mmol, purchased) were added into ultra-dry dichloromethane (70 ml). Propylphosphoric anhydride (39.6 g, 62.2 mmol, 50% in EA) was added, and the mixture was cooled down to 0° C. After N,N-diisopropylethylamine (16 g, 124.4 mmol) was added dropwise, the reaction was completed by stirring at room temperature for four hours. Then, the solution was cooled down to 0° C., 200 ml of 1 M sodium dihydrogen phosphate aqueous solution was added dropwise, extracted with dichloromethane (100 ml*3), dried, concentrated, and separated by columns. Flash column, 200-300 mesh silica gel, petroleum ether:ethyl acetate (18~40% EA product), m=6.0 g, yellowish-brown solid, yield=94.2%. $^{1}$H-NMR (400 MHz, $CDCl_3$): δ7.28-7.48 (m, 6H), 7.68-7.02 (m, 3H), 5.08 (s, 2H). MS: 262.2[$(M+1)^+$], Synthesis of AST-3424-D6-F Under nitrogen protection, AST-3424-D6-E (5 g, 19.2 mmol) was dissolved in absolute ethanol (50 ml). Palladium-carbon catalyst (2.5 g) was added, and the mixture was stirred at room temperature overnight. After the reaction was completed, nitrogen was replaced, and suction filtered. The palladium-carbon in the mixture was washed with absolute ethanol, and then a pure product was obtained after concentration. m=3.1 g, white solid, yield 93.9%. $^{1}$H-NMR (400 MHz, $CDCl_3$): δ8.05 (brs, 1H), 7.16-7.20 (m, 1H), 6.97-6.98 (m, 1H), 6.83-6.84 (m, 1H), 6.81-6.82 (m, 1H). MS: 172.2 [$(M+1)^+$].

Synthesis of AST-3424-D6-I

Under nitrogen protection, phosphoryl chloride (1.2 ml, 12.98 mmol) was added to anhydrous dichloromethane (10 ml). After cooling to 40° C., AST-3424-D6-H (1.2 g, 6.49 mmol, commercially available) in dichloromethane solution (10 ml) was added to the mixture dropwise slowly. Next, a solution of trimethylamine (1.7 g, 16.87 mmol) in dichloromethane (10 ml) was added dropwise at −40° C. for six hours to complete the conversion of the raw materials. 2-bromoethylamine hydrobromide (10.7 g, 52 mmol) was added at −40° C. Then, a solution of trimethylamine (5.3 g, 52 mmol) in dichloromethane (20 ml) was added dropwise at −40° C. for 30 minutes. The mixture was naturally raised to room temperature and stirred overnight. After the reaction was completed, the temperature was cooled down to 0° C. 10% potassium carbonate aqueous solution (10 ml) was added dropwise and stirred for 5 minutes. The mixture was extracted with dichloromethane (15 ml*3), dried, concentrated, separated by columns (200-300 mesh silica gel, washed with EA to obtain a product 1.3 g, 42.0%) to obtain a yellow oily liquid. $^{1}$H-NMR (400 MHz, $CDCl_3$): δ8.05-8.09 (m, 1H), 7.28-7.33 (m, 2H), 5.53-5.57 (m, 1H), 3.49-3.52 (m, 2H), 3.31-3.42 (m, 4H), 3.18-3.24 (m, 4H), 1.61 (d, J=6.4 Hz, 3H) MS: 477.9[$(M+1)^+$].

Synthesis of AST-3424-D6-J

Under nitrogen protection, AST-3424-D6-I (1.0 g, 2.1) was dissolved in THF (20 ml), and silver oxide (5.8 g, 25.2 mmol) an DIEA (1.4 g, 10.5 g) were added. Next, after the mixture was heated to reflex for 2 hours, the heated mixture was suction filtered, washed with THF (10 ml), removed the solvents, and separated by columns (200-300 mesh, 80-100% ethyl acetate in heptane solution) to obtain AST-3424-D6-J, a yellow liquid. $^{1}$H-NMR (400 MHz, $CDCl_3$): δ7.98-8.02 (m, 1H), 7.20-7.30 (m, 2H), 5.58-5.65 (m, 1H), 2.00-2.17 (m, 8H), 1.56 (d, J=6.8 Hz, 3H). MS: 316.1[$(M+1)^+$].

Synthesis of AST-3424-D6

Under nitrogen protection, AST-3424-D6-J (100 mg, 0.32 mmol) and AST-3424-D6-F (81 mg, 0.48 mmol) were dissolved in dry DMF (5 ml), and then potassium carbonate (87 mg, 0.63 mmol) was added. After stirring at room temperature overnight, ethyl acetate (60 ml) was added to dilute. Then, the mixture was washed with water (3*5 ml), wash with brine (3*5 ml), dried with anhydrous sodium sulfate, removed the solvent, and separated by columns (200-300 mesh, DCM:MeOH=50:1) to obtain AST-3424-D6, a yellow oily liquid. $^{1}$H-NMR (400 MHz, $CDCl_3$): δ7.98-8.02 (m, 1H), 7.20-7.30 (m, 2H), 5.58-5.65 (m, 1H), 2.00-2.17 (m, 8H), 1.56 (d, J=6.8 Hz, 3H). MS: 467.1 [$(M+1)^+$].

In a similar route, the compound of structural formula II with R-configuration can be synthesized after replacing an original compound with AST-3424-D6-H.

What is claimed is:

1. An orally administered solid dosage form for treating cancers, tumors or cell proliferative disorders, the orally administered solid dosage form comprising a compound having structural formula I or II as follow:

I

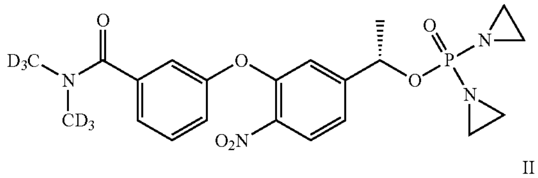

II

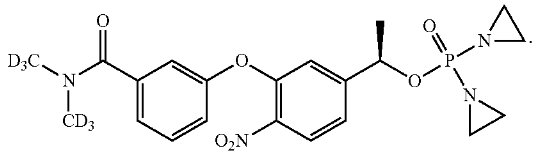

2. The solid dosage form of claim 1, wherein the solid dosage form is a tablet.

3. The solid dosage form of claim 2, wherein the tablet comprises at least one alkaline agent selected from the group consisting of $Na_2CO_3$, $NaHCO_3$, NaOH, and $KH_2PO_4$, so that the tablet is dissolved or dispersed in water to form an aqueous solution or an aqueous dispersion having a pH value greater than 6.8.

4. The solid dosage form of claim 2, wherein the tablet comprises the compound having structural formula I or II and pharmaceutical excipients.

5. The solid dosage form of claim 1, wherein the solid dosage form is an enteric-coated tablet.

6. The solid dosage form of claim 5, wherein the enteric-coated tablet comprises an enteric coating and a tablet core, and the tablet core comprises the compound having structural formula I or II and pharmaceutical excipients.

7. The solid dosage form of claim 1, wherein the solid dosage form is an enteric capsule.

8. The solid dosage form of claim 7, wherein the enteric capsule comprises an enteric-coated capsule shell and a mixture filled in the enteric-coated capsule shell, wherein the mixture comprises the compound having structural formula I or II and pharmaceutical excipients.

9. The solid dosage form of claim 8, wherein the mixture is in a form of granules.

10. The solid dosage form of claim 8, wherein the enteric capsule comprises a soft enteric-coated capsule shell, and wherein the mixture is a solution, and a concentration of the compound having structural formula I or II in the solution is 1-270 mg/ml.

11. The solid dosage form of claim 10, wherein the solution comprises a solvent mixture of ethanol and propylene glycol.

12. The solid dosage form of claim 11, wherein the solvent mixture comprises at least 50% of ethanol by volume.

13. The solid dosage form of claim 12, wherein the solvent mixture is composed of 75% of ethanol and 25% of propylene glycol by volume.

14. The solid dosage form of claim 10, wherein no water is added to the solution, and a content of the water is controlled within 0.5% by mass.

15. The solid dosage form of claim 1, wherein the tumors, the cancers, or the proliferative disorders are selected from the group consisting of lung cancer, non-small cell lung cancer, liver cancer, pancreatic cancer, stomach cancer, bone cancer, esophagus cancer, breast cancer, prostate cancer, testicular cancer, colon cancer, ovarian cancer, bladder cancer, cervical cancer, melanoma, squamous-cell cancer, basal cell carcinoma, adenocarcinoma, squamous-cell carcinoma, sebaceous carcinoma, papillary carcinoma, papillary adenocarcinoma, cystadenocarcinoma, cystic carcinoma, medullary carcinoma, bronchial carcinoma, bone cell carcinoma, epithelial carcinoma, cholangiocarcinoma, choriocarcinoma, embryonic carcinoma, seminoma, Wilms' carcinoma, glioblastoma, astrocytoma, medulloblastoma, craniopharyngioma, ependymoma, pineal tumor, hemoblastoma, neurogenic tumor of the larynx, meningiomas, neuroblastoma of optic nerve, neuroblastomas, retinoblastomas, neurofibromas, fibroma sarcomatosum, fibroblastomas, fibroma, fibroadenomas, fibrochondromas, fibrocystic tumors, fibrous myxoma, osterfibroma, myxofibrosarcoma, fibropapillary, myxofibrosarcoma, bursal tumor, myxonchondroma, myxonchondrosarcoma, myxedema, myxoblastoma, liposarcoma, lipoma, lipoadenoma, lipoblastoma, lipochondroma, lipofibroma, lipoangioma, myxolipoma, chondrosarcoma, chondroma, chondromyoma, chordoma, chorioadenoma, chorioepithelioma, chorioblastoma, osteosarcoma, osteoblastoma, osteochondrofibroma, osteochondrosarcoma, osteochondroma, osteocystoma, cementoma, osteofibroma, fibrosarcoma, angiosarcoma, hemangioma, angiolipoma, angiochondroma, hemangioblastoma, angiokeratoma, angioglioma, hemangioendothelioma, angiofibroma, angiomyoma, angiolipoma, angiolymphoma, angiolipiomyoma, angiomyolipomas, angiomyoneuroma, angiomyxoma, angioreticuloendothelioma, lymphangiosarcoma, lymphogranuloma, lymphangioma, lymphoma, lymphomyxoma, lymphosarcoma, lymphangial fibrom, lymphocytoma, lymphoepithelioma, lymphoblastoma, endothelioma, endothelioblastoma, synovialoma, synovial sarcoma, mesothelioma, desmoplastic tumor, Ewing's tumor, leiomyoma, leiomyosarcoma, leioblastoma, leiomyofibroma, rhabdomyoma, rhabdomyosarcoma, rhabdomyomatous myxoma, acute lymphoblastic leukemia, acute myeloid leukemia, chronic disease cells, polycythemia, lymphoma, endometrial cancer, glioma, colorectal cancer, thyroid cancer, urothelial cancer or multiple myeloma.

16. A preparation method of the solid dosage form of claim 1, the method comprising:

mixing pharmaceutical excipients, an ethanol solution of the compound having the structural formula I or II of claim 1, and water to form a mixture;

granulating the mixture to form granulates;

directly tableting the granulates to obtain a tablet; and coating the tablet to obtain an enteric-coated tablet.

17. A compound having structural formula I or II:

I

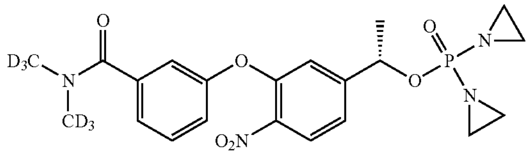 [SMILES: [2H]C([2H])([2H])N(C(=O)c1cccc(Oc2cc([C@H](C)OP(=O)(N3CC3)N3CC3)ccc2[N+](=O)[O-])c1)C([2H])([2H])[2H]]

II

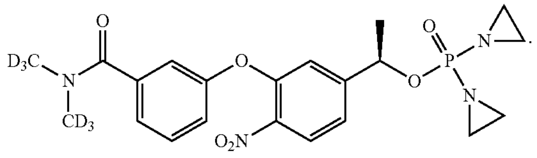

18. A method of treating a subject having cancers, tumors or cell proliferative disorders, the method comprising orally administering to the subject in need thereof an effective dosage of the solid dosage form of claim 1.

19. The method of claim 18, wherein a minimum administrable dosage unit of the solid dosage form comprises 0.2 mg, 0.5 mg, or 1.0 mg of the compound having structural formula I or II.

20. A method of preparing the compound of claim 17, the method comprising reacting compounds III and IV with a compound V:

III

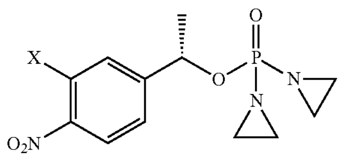

-continued
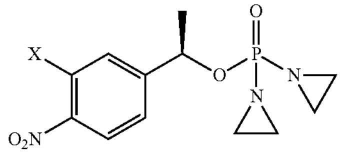
IV
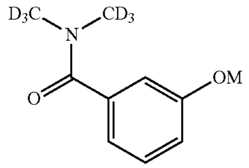
V
wherein X is a halogen atom, and
M is H, an alkali metal or an alkaline earth metal.
21. The solid dosage form of claim 6, wherein the pharmaceutical excipients comprise at least one of $Na_2CO_3$, $NaHCO_3$, NaOH, and $KH_2PO_4$.
22. The solid dosage form of claim 8, wherein the pharmaceutical excipients comprise at least one of $Na_2CO_3$, $NaHCO_3$, NaOH, and $KH_2PO_4$.
* * * * *